(12) United States Patent
Okumura et al.

(10) Patent No.: US 12,150,643 B2
(45) Date of Patent: Nov. 26, 2024

(54) ENDOSCOPIC TREATMENT DEVICE

(71) Applicant: OLYMPUS CORPORATION, Tokyo (JP)

(72) Inventors: Takuya Okumura, Hamburg (DE); Kunihide Kaji, Hachioji (JP); Nobuko Matsuo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 508 days.

(21) Appl. No.: 17/574,848

(22) Filed: Jan. 13, 2022

(65) Prior Publication Data
US 2022/0133295 A1 May 5, 2022

Related U.S. Application Data

(63) Continuation of application No. PCT/JP2019/027894, filed on Jul. 16, 2019.

(51) Int. Cl.
*A61B 17/08* (2006.01)
*A61B 17/04* (2006.01)
*A61B 17/00* (2006.01)

(52) U.S. Cl.
CPC ...... *A61B 17/0482* (2013.01); *A61B 17/0469* (2013.01); *A61B 17/08* (2013.01);
(Continued)

(58) Field of Classification Search
CPC . A61B 17/0482; A61B 17/0469; A61B 17/08; A61B 2017/00818; A61B 2017/0472;
A61B 2017/081; A61B 17/062; A61B 2017/0034; A61B 2017/00358; A61B 17/083; A61B 2017/00269;
(Continued)

(56) References Cited

U.S. PATENT DOCUMENTS 4,177,802 A 12/1979 Ogami
4,753,237 A 6/1988 Puchy
(Continued)

FOREIGN PATENT DOCUMENTS

JP 01-122711 U 8/1989
JP 2003-532480 A 11/2003
(Continued)

OTHER PUBLICATIONS

Chinese Office Action dated Sep. 23, 2023 received in 201980098433.6.
(Continued)

*Primary Examiner* — Mohamed G Gabr
*Assistant Examiner* — Aman Kumar Mann
(74) *Attorney, Agent, or Firm* — Scully, Scott, Murphy & Presser, P.C.

(57) ABSTRACT

A tissue traction device includes a first needle connected to a distal end of a first thread; a second needle connected to a distal end of a second thread; an elongated main body connected to the first thread and extending between the first thread and the second thread, the main body being elastically deformable; a tube disposed at a proximal end of the main body; and a traction member having a distal end connected to a distal end portion of the main body, the traction member extending from the distal end portion of the main body toward a distal end of the tube.

18 Claims, 28 Drawing Sheets

(52) U.S. Cl.
 CPC ............ *A61B 2017/00818* (2013.01); *A61B 2017/0472* (2013.01); *A61B 2017/081* (2013.01)

(58) Field of Classification Search
 CPC . A61B 2017/0608; A61B 17/02; A61B 17/04; A61B 2017/0618; A61B 90/02; A61B 90/00; A61B 2017/086; A61B 2017/08
 See application file for complete search history.

(56) References Cited

U.S. PATENT DOCUMENTS

| | | | | |
|---|---|---|---|---|
| 4,798,205 | A | * | 1/1989 | Bonomo ............... A61M 29/02 128/897 |
| 5,458,609 | A | * | 10/1995 | Gordon ............... A61B 17/0625 606/147 |
| 2004/0147941 | A1 | * | 7/2004 | Takemoto ........... A61B 17/0483 606/144 |
| 2012/0130389 | A1 | * | 5/2012 | Prywes ............... A61F 9/00736 606/107 |
| 2015/0142040 | A1 | * | 5/2015 | Kawaura ............ A61B 17/3468 606/185 |

FOREIGN PATENT DOCUMENTS

| | | |
|---|---|---|
| JP | 2007-282841 A | 11/2007 |
| JP | 4805293 B2 | 11/2011 |
| JP | 2014-100344 A | 6/2014 |
| WO | 01/85035 A2 | 11/2001 |

OTHER PUBLICATIONS

International Search Report dated Aug. 27, 2019 received in PCT/JP2019/027894.

* cited by examiner

ENDOSCOPIC TREATMENT DEVICE

The present application is a continuation application of PCT International Application No. PCT/JP2019/027894, filed on Jul. 16, 2019. The content of the above-identified PCT International Applications is incorporated herein by reference.

TECHNICAL FIELD

The present disclosure relates to an endoscopic treatment device.

BACKGROUND ART

There are procedures to remove a part of the stomach wall using an endoscope and a treatment device passing through the endoscope. According to the Endoscopic Submucosal Dissection (ESD), a relatively large area of the mucosal layer and a portion of the submucosal layer are dissected so as to result in a tissue deficient area. According to the Endoscopic Full-thickness Resection (EFTR), a relatively large area of the stomach wall is resected over the entire layer so as to create an opening in the stomach wall.

In order to complete the procedures, it is necessary to suture and close the tissue deficient area including the opening (hereinafter referred to as "opening"). The closing procedures are performed by hooking a thread on two sites of the surrounding tissue around the opening and then pulling the thread so as to gather the two sites where the thread is hooked close to each other. When the area of the opening is large, the distance between the two sites becomes large, and the movement amount of the needle for hooking the thread also becomes large. In a case in which the opening is large, it is necessary to hook the thread at more sites. Accordingly, it is not easy to close the opening with a treatment device protruding from the endoscope.

As a method of closing the opening, a method of using a plurality of clips as described in Japanese Patent (Granted) Publication No. 4805293 is also known. Even when the opening is closed with the clips described in Japanese Patent (Granted) Publication No. 4805293, it is necessary to hook the arm at two sites in the surrounding tissues around the opening. However, the arm is slippery with respect to the tissue, and a reaction force is generated when pulling the tissue such that it takes the same or more effort to close the opening as when hooking the threads.

SUMMARY

According to an aspect of the present disclosure, a tissue traction device includes a first needle connected to a distal end of a first thread; a second needle connected to a distal end of a second thread; an elongated main body connected to the first thread and extending between the first thread and the second thread, the main body being elastically deformable; a tube disposed at a proximal end of the main body; and a traction member having a distal end connected to a distal end portion of the main body, the traction member extending from the distal end portion of the main body toward a distal end of the tube.

According to another aspect of the present disclosure, a tissue traction device includes a first thread; a second thread; an elongated main body connected to the first thread and extending between the first thread and the second thread, the main body being elastically deformable; a tube disposed at a proximal end of the main body; and a traction member having a distal end connected to a distal end portion of the main body, the traction member extending from the distal end portion of the main body toward a distal end of the tube, wherein the first thread includes a first ring, and the second thread includes a second ring that protrudes from the tube.

DESCRIPTION OF EMBODIMENTS

A first embodiment of the present disclosure will be described with reference to FIGS. 1 to 10.

Figure 1:
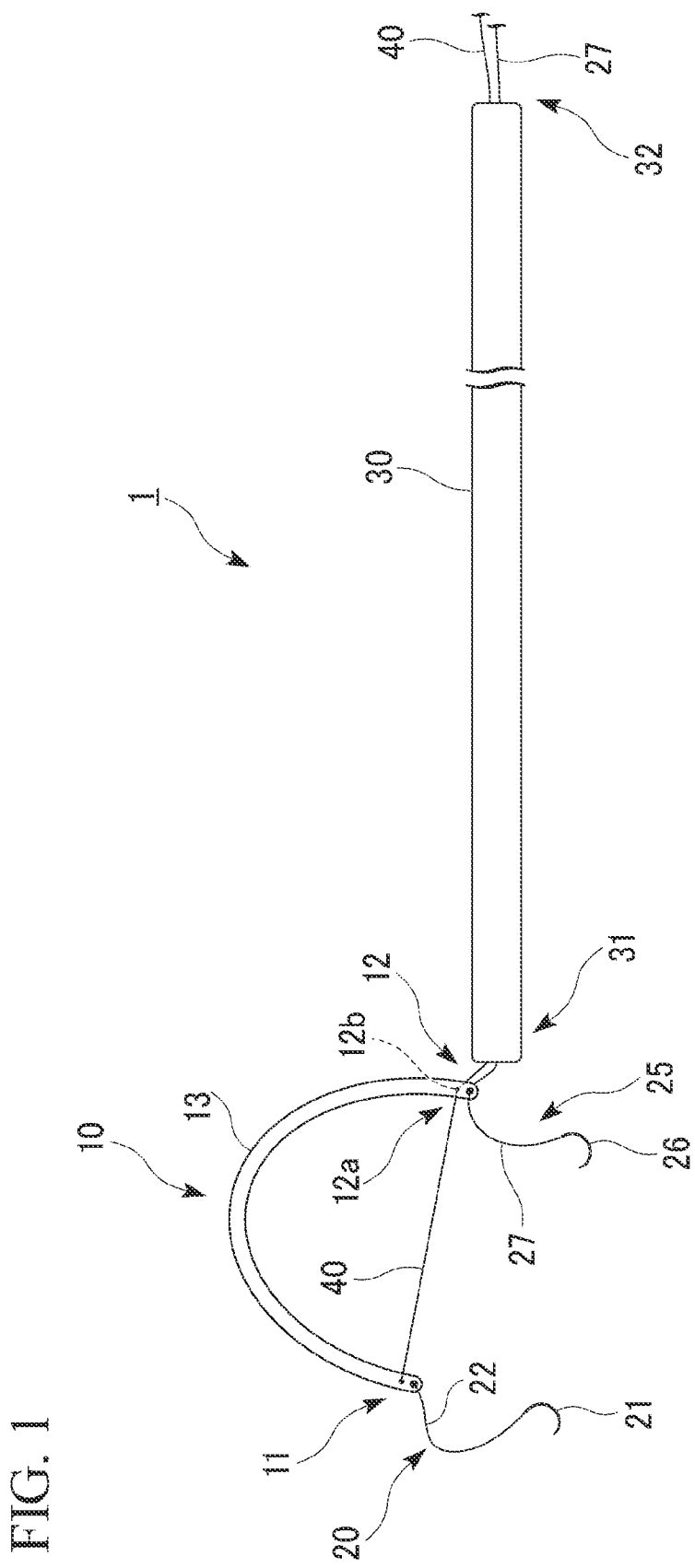
FIG. 1 is an overall view showing a tissue traction device according to a first embodiment of the present disclosure.

FIG. 1 is an overall view of a tissue traction device 1 according to the present embodiment. The tissue traction device 1 is an endoscopic treatment device including an elongated main body 10, two fixing elements as a first fixing element 20 and a second fixing element 25 provided at both ends of the main body 10, and a sheath (tube) 30 provided on the proximal end side of the main body 10.

The main body 10 is made of resin, metal, or the like and is formed in an elongated shape such as a rod shape, a strip shape, or a tubular shape. The main body 10 has a distal end portion 11, a proximal end portion 12, and an intermediate portion 13 between the distal end portion 11 and the proximal end portion 12. The intermediate portion 13 is bent in an arc shape (first bent shape, initial shape) in a natural state where no external force is applied thereto, and the intermediate portion 13 is apart away from a straight line connecting the distal end portion 11 and the proximal end portion 12. The main body 10 has flexibility. Accordingly, the main body 10 may be configured to deform the intermediate portion 13 into a second bent shape having a smaller curvature radius than that of the first bent shape by elastically deforming the distal end portion 11 and the proximal end portion 12 to approach each other. The intermediate portion 13 deformed into the second curved shape generates a restoring force to return to the first bent shape. The restoring force is applied to separate the closing distal end portion 11 and the proximal end portion 12 from each other.

The first fixing element 20 has a first needle 21 and a first thread 22. The first needle 21 is a bent needle, the first needle 21 is connected to the distal end of the first thread 22, and the proximal end of the first thread 22 is connected to the main body 10.

The second fixing element 25 has a second needle 26 and a second thread 27. The second needle 26 is also a bent needle. The second needle 26 is connected to the distal end of the second thread 27, and the proximal end of the second thread 27 is inserted into a hole 12a of the main body 10 (shown enlarged in FIG. 2) to be freely advanceable and retractable. The main body 10 and the second thread 27 are connected to each other. The main body 10 extends between the proximal end of the first thread 22 and the proximal end of the second thread 27.

A traction member 40 for deforming the main body 10 is attached to the distal end portion 11 of the main body 10. The traction member 40 is an elongated member, and the traction member 40 is passed through a hole 12b formed in the proximal end portion 12 of the main body 10. The traction member 40 is slidable in the hole 12b. The traction member 40 may be passed through the hole 12a without forming the hole 12b in the main body 10.

The sheath 30 is a flexible tubular member and has lumens extending along a longitudinal axis. The second thread 27 and the traction member 40 can independently advance and retreat with respect to the sheath 30. As shown in FIG. 1, the second thread 27 and the traction member 40 are preferably arranged to enter the sheath 30 through the distal end opening 31 of the sheath 30 and exit from the proximal opening 32 through the lumen (hole) of the sheath 30. Instead of the lumen, a guide hole through which the second thread 27 passes may be formed only at the distal end portion of the sheath 30. Similarly, the guide hole through which the traction member 40 passes may be formed only at the distal end portion of the sheath 30. In this case, each of the second thread 27 and the traction member 40 may pass through the guide hole, and the second thread 27 and the traction member 40 coming out from the guide hole may be arranged to come out from the forceps port via the channel of the endoscope. Also, a configuration in which either of the second thread 27 or the traction member 40 passes through the guide hole may be provided.

The operations when the tissue traction device 1 having the above-described configuration according to the present embodiment is used will be described. In the following description, an example will be taken in which a part of the wall of a luminal organ such as the stomach is completely resected by EFTR or the like.

First, a user introduces the tissue traction device 1 together with the endoscope into the body as the treatment target.

Figure 2:
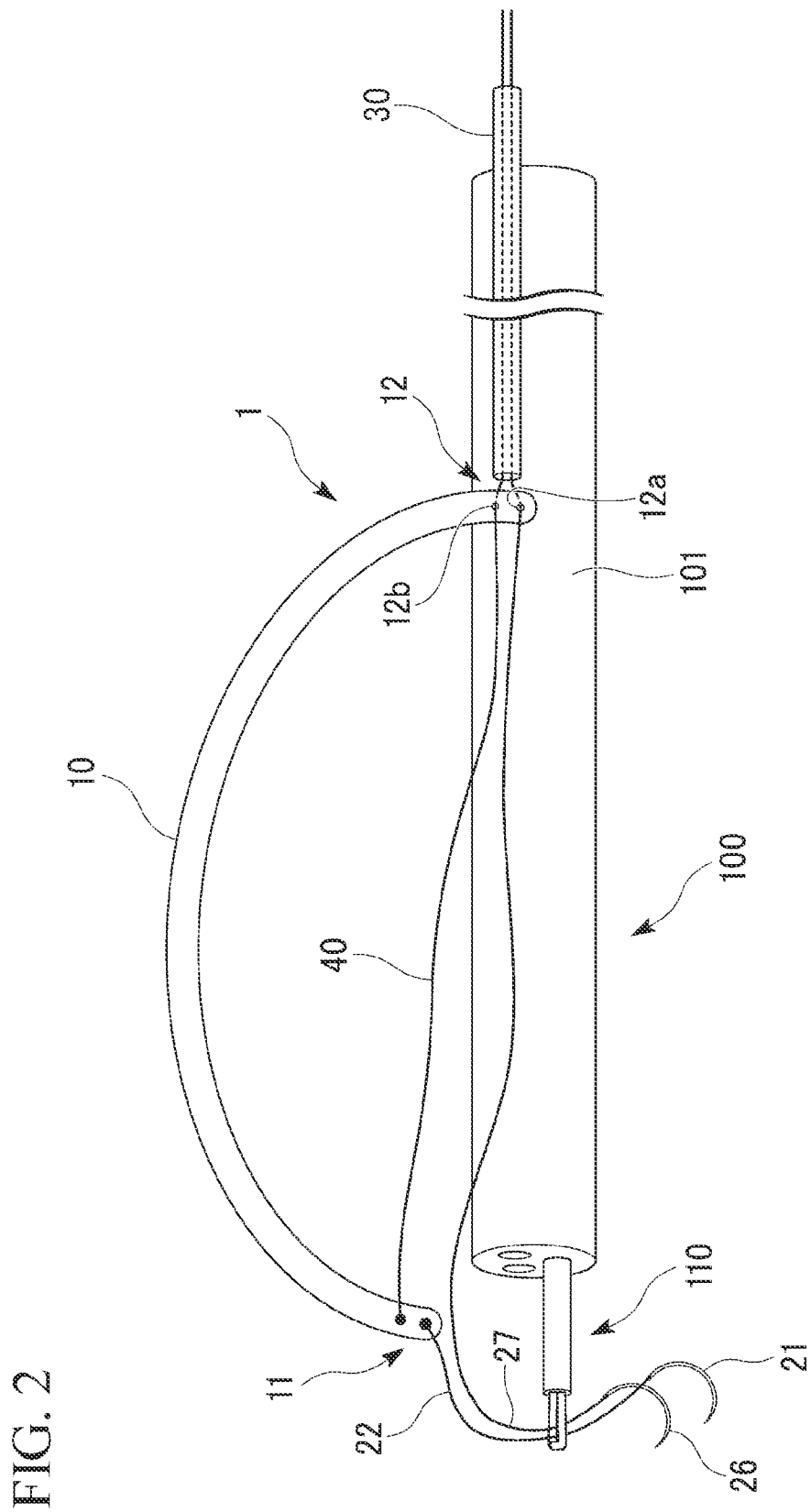
FIG. 2 is a view showing the tissue traction device when being introduced into the body together with an endoscope.

FIG. 2 shows an example of the endoscope 100 and the tissue traction device 1 when being introduced into the body. The endoscope 100 and the tissue traction device 1 are introduced into the body through the mouth or the like while the main body 10 is placed along the insertion portion 101 of the endoscope 100 in a state in which the two fixing elements are grasped by the forceps 110 or the like inserted into the endoscope 100.

In FIG. 2, the first thread 22 and the second thread 27 are grasped by the forceps 110; however, the first needle 21 and the second needle 26 may be grasped. A cap may be attached to the distal end of the endoscope 100, and the first needle 21 and the second needle 26 may be positioned in the cap and then introduced into the body.

Figure 3:
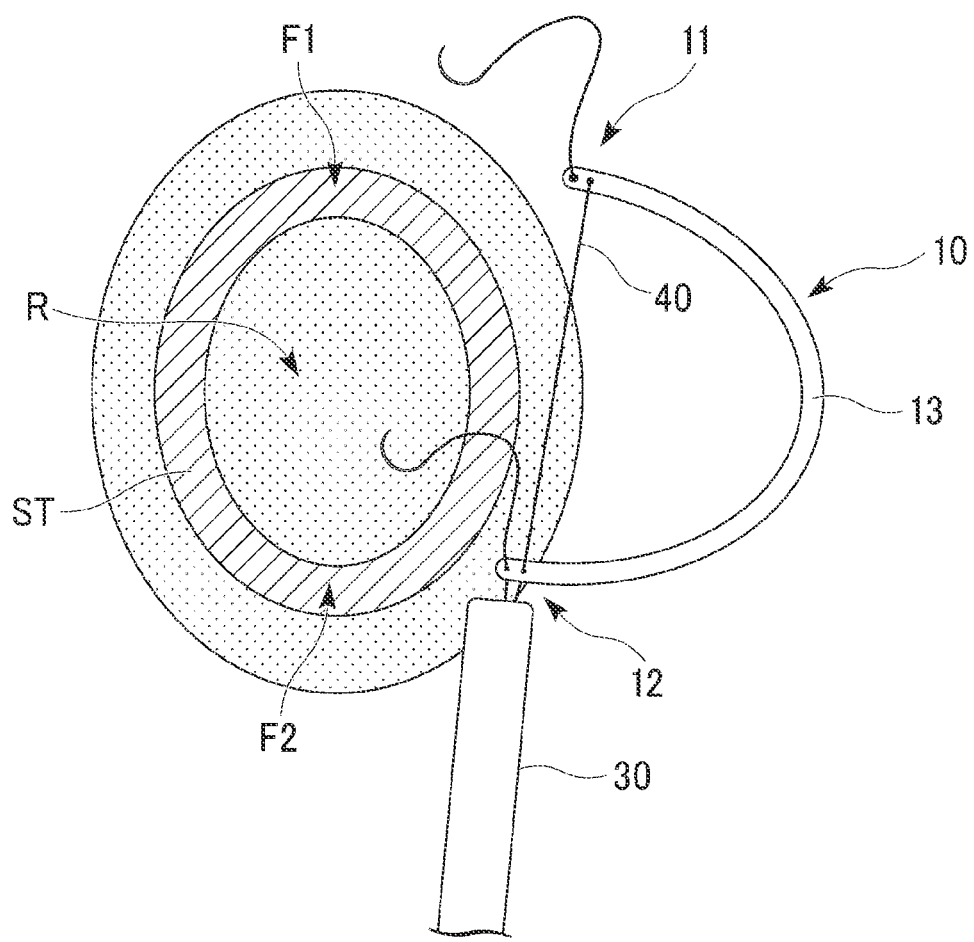
FIG. 3 is a view showing a procedure of the full-thickness resection with respect to the gastrointestinal tract using the present tissue traction device.
Figure 4:
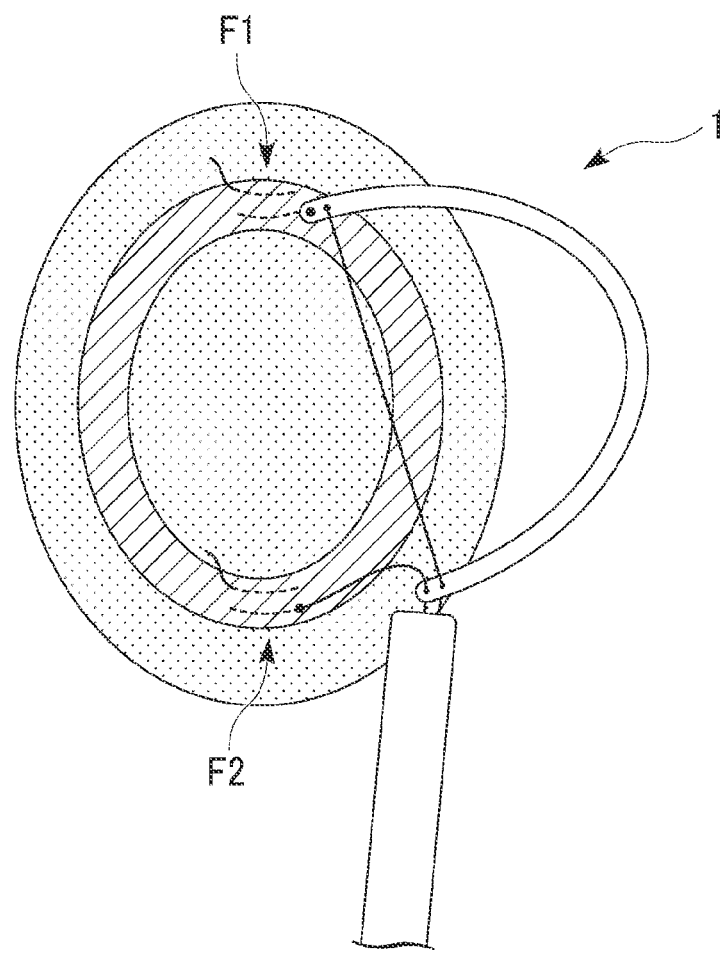
FIG. 4 is a view showing a procedure of the full-thickness resection with respect to the gastrointestinal tract using the present tissue traction device.
Figure 5:
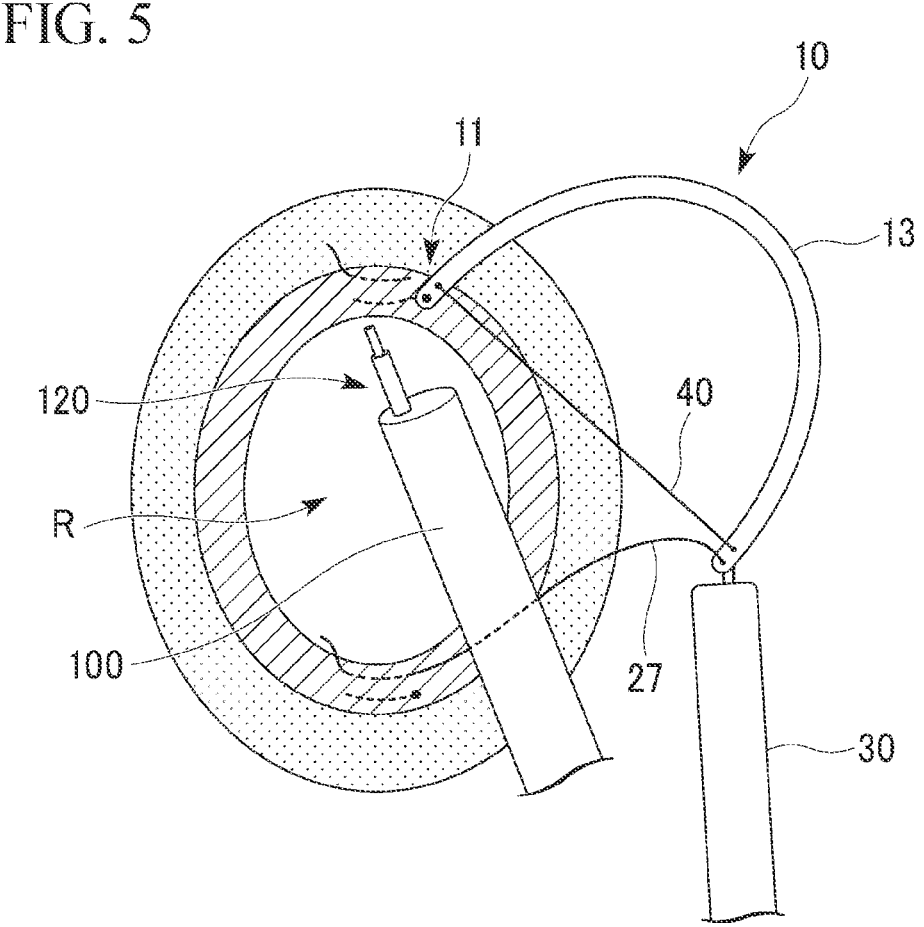
FIG. 5 is a view showing a procedure of the full-thickness resection with respect to the gastrointestinal tract using the present tissue traction device.

The user confirms the main body 10 with the endoscope 100, and when the distal end of the sheath 30 is apart away from the main body 10, the distal end of the sheath 30 is brought into contact with the proximal end portion 12 of the main body 10. Furthermore, as shown in FIG. 3, the user pulls the traction member 40 (retracts the traction member 40 with respect to the sheath 30) while holding the sheath 30 in a state in which the distal end of the sheath 30 is in contact with the proximal end portion 12 such that the distal end portion 11 is moved to approach the proximal end portion 12 side. As a result, the intermediate portion 13 of the main body 10 is elastically deformed into the second bent shape, and a restoring force tending to return to the first bent shape is generated in the main body 10. The user holds the sheath 30 and the traction member 40 to maintain the second bent shape.

The user confirms the region R to be resected by using the endoscope 100, and determines the positions of two fixation sites for fixing the fixing elements in the surrounding tissues ST around the region R. If the fixation sites are set one by one at positions sandwiching the region R in the advancement and retraction direction of the endoscope 100, the procedures of closing the opening thereafter can be easily performed. The distance between the two fixation sites is set to be shorter than the distance between the distal end portion 11 and the proximal end portion 12 in the main body 10 in the natural state (first bent shape).

Next, the user hooks the first needle 21 at the fixation site F1 (first fixation site) on the back side (the position farther from the endoscope 100) by the forceps such as a needle holder protruding from the endoscope 100 and locks the first thread 22 to the fixation site F1. Further, the user uses the forceps to hook the second needle 26 on the other fixation site F2 (second fixation site), and the second thread 27 is locked to the fixation site F2.

As described above, as shown in FIG. 4, the attachment of the tissue traction device 1 to the gastrointestinal wall has been finished. Either of the fixation of the fixing element to the fixation site F1 or the fixation of the fixing element to the fixation site F2 may be performed at first. In the case of performing the EFTR, if a part of the gastrointestinal tract is dissected and an opening (described later) is formed, the gastrointestinal tract is deflated and it becomes difficult to fix the gastrointestinal tract. Accordingly, it is preferable to perform the attachment of the tissue traction device 1 to the gastrointestinal wall (locking by the first thread 22 and the second thread 27) before performing the full-thickness resection.

Next, the user performs the full-thickness resection with respect to the region R using a high-frequency knife 120 or the like. Since the main body 10 is deformed into the second bent shape, even if the first thread is fixed to the fixation site F1, it is still difficult for the first thread to extend over the region R and it is difficult for the main body 10 to interfere with the full-thickness resection procedures.

Figure 10:
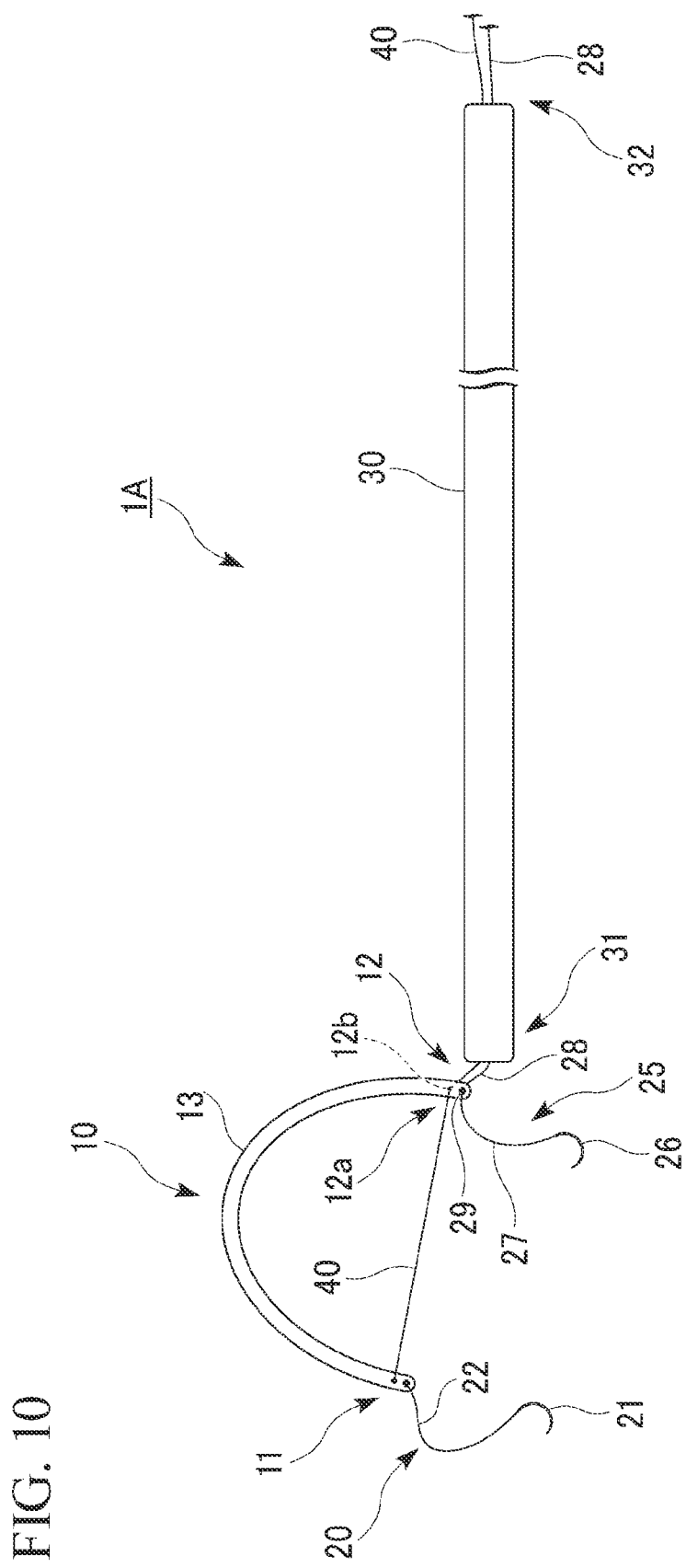
FIG. 10 is a view showing a tissue traction device according to a modification example of the first embodiment.

When the user advances the sheath 30 while holding a part (operation portion) of the sheath 30 and the traction member 40 located outside the body while not holding the second thread 27, as shown in FIG. 10, the main body 10 rotates around the distal end portion 11 to further move the intermediate portion 13 and the traction member 40 away from the region R.

By the full-thickness resection procedures, an opening Op is formed in the region R. In a case in which the target procedure is ESD, a bottomed opening is formed in the region R where the mucosal layer is resected together with a part of the submucosal layer.

Figure 6:
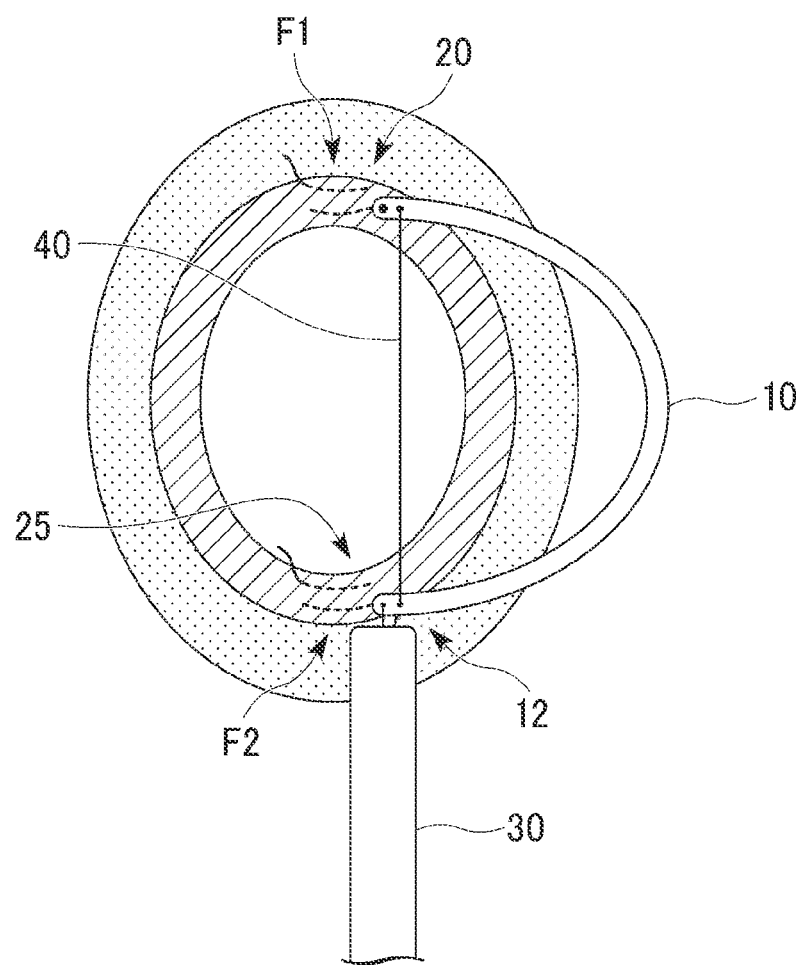
FIG. 6 is a view showing a procedure of the full-thickness resection with respect to the gastrointestinal tract using the present tissue traction device.
Figure 7:
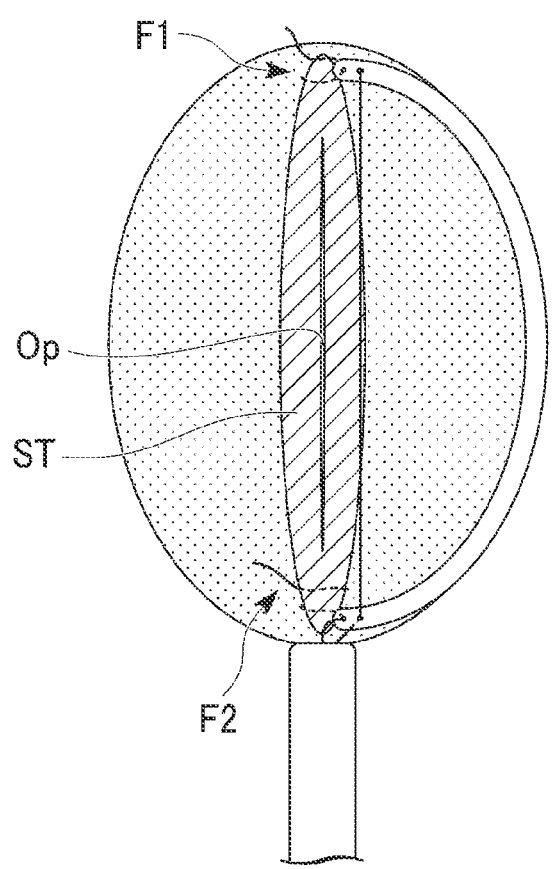
FIG. 7 is a view showing a procedure of the full-thickness resection with respect to the gastrointestinal tract using the present tissue traction device.

When the user pulls the second thread 27 while maintaining the positional relationship between the sheath 30 and the traction member 40, the proximal end portion 12 of the main body 10 approaches the fixation site F2, as shown in FIG. 6. Thereafter, when the user advances the traction member 40, the main body 10 tends to return to the first bent shape by the above-mentioned restoring force. This restoring force is applied from the first fixing element 20 and the second fixing element 25 to the fixation site F1 and the fixation site F2, respectively. As a result, the fixation site F1 and the fixation site F2 move to be separated from each other. As the fixation site F1 and the fixation site F2 are separated from each other, as shown in FIG. 7, the opening Op is elongatedly stretched and deformed in the direction connecting the fixation site F1 and the fixation site F2 such that the surrounding tissues ST being opposite to each other and sandwiching the opening Op approach each other. The main body 10 maintains the state in which the opening Op is stretched against the reaction force received from the tissues.

Figure 8:
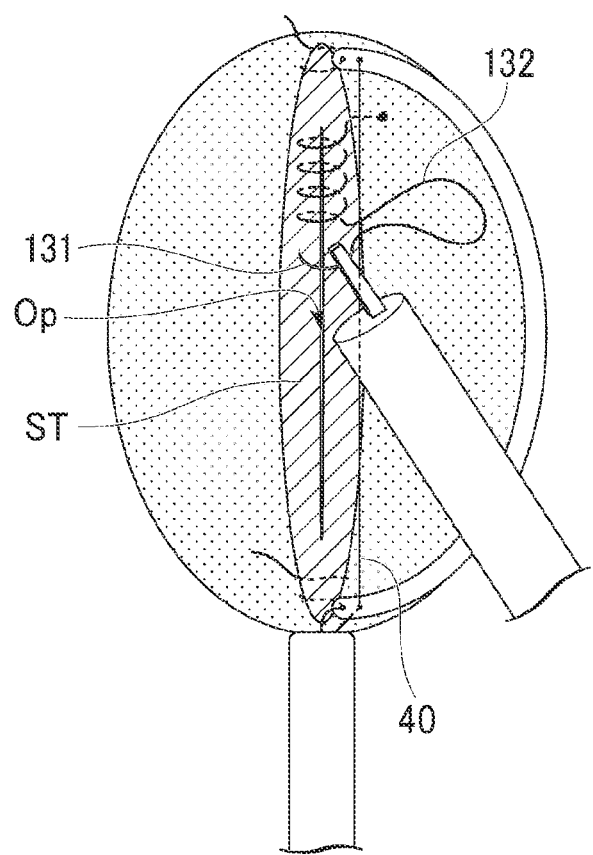
FIG. 8 is a view showing a procedure of the full-thickness resection with respect to the gastrointestinal tract using the present tissue traction device.

As shown in FIG. 8, the user sutures and closes the opening Op using a needle 131 and a thread 132 separately introduced into the body while maintaining the stretched state of the opening Op. Since the opening Op is stretched, the surrounding tissues ST around the opening Op is close to each other such that the needle can be hooked on the surrounding tissues ST of the opening Op with a small movement amount of the needle, and it becomes easier to perform the suture than the conventional configuration.

Instead of the needle 131 and the thread 132, other medical devices such as clips and staplers may be used to close the opening Op. In a case in which it is difficult to perform the suture procedures, the user may cut off the traction member 40.

Figure 9:
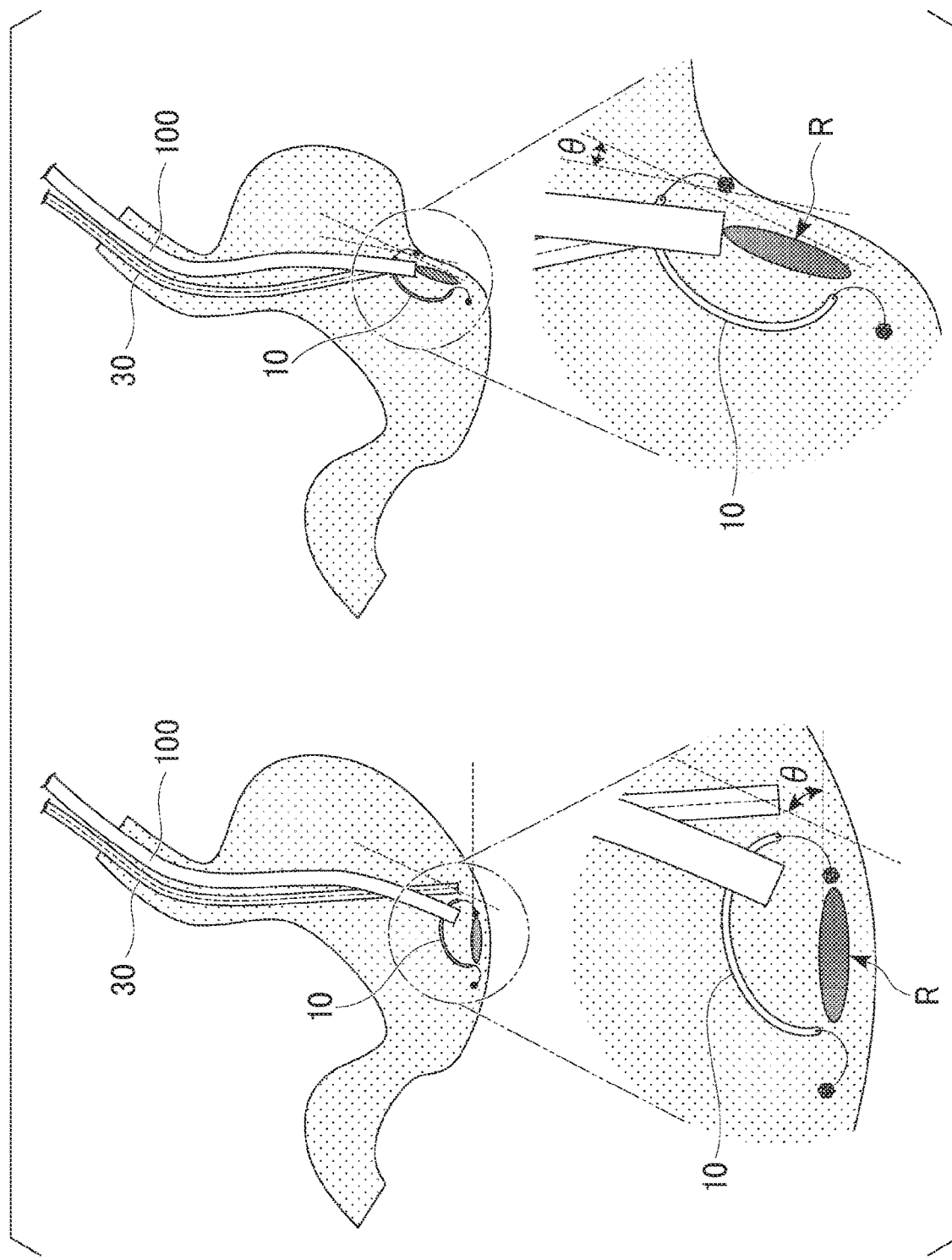
FIG. 9 is a view showing an example of an angle adjustment operation between the tissues to be sutured and the endoscope.

As shown in FIG. 9, when the second thread 27 is pulled, the treatment site to which the main body 10 is attached can be pulled toward the mouth side. Such operations are useful for adjusting an angle $\theta$ formed by the tangential direction of the tissues of the luminal wall as the closing target and the longitudinal axis of the forceps protruding from the endoscope 100.

After the opening Op has been closed by the suturing, the user cuts off the first thread 22 and the second thread 27 to separate the tissue traction device 1 from the gastrointestinal tract. Finally, the entire tissue traction device 1 including the first needle 21 and the second needle 26 is removed from the body together with the endoscope 100 to complete the series of procedures.

The first needle 21 and the second needle 26 may be recovered immediately after the attachment of the tissue traction device 1 to the gastrointestinal wall is completed.

As described above, the tissue traction device 1 according to the present embodiment is configured to make the first fixing element 20 and the second fixing element 25 provided at both ends of the main body 10 to be fixed at the two fixation sites around the region to be resected, and it is possible to elongatedly stretch the region after forming the opening and the resection by the restoring force generated in the main body 10 to gather the surrounding tissues around the region close to each other. As a result, the procedures for closing the opening can be performed more easily than the conventional operations.

The tissue traction device 1A according to a modification example shown in FIG. 10 has a configuration in which an evacuation thread 28 for operation is connected to the second thread 27. The evacuation thread 28 is an elongated member, and for example, preferable to be a wire or a thread. According to the present modification example, the second thread 27 is short, and the second thread 27 and the evacuation thread 28 are connected at a knot 29. The evacuation thread 28 is passed through the hole 12a of the main body 10, and the knot 29 has is configured to have a dimension that the knot 29 cannot pass through the hole 12a.

In the tissue traction device 1A, the second thread 27 and the main body 10 are not connected, however, the opening can be elongatedly stretched by almost the same operations as that by the tissue traction device 1. Furthermore, when the proximal end portion of the main body 10 comes into contact with the knot 29, the proximal end portion of the main body 10 does not move any further, such that it is possible to prevent the main body from pressing against the tissues more than necessary.

According to the present embodiment, the sheath and the traction member are not essential. For example, in a state in which the second thread is fixed to the tissue, the main body may be elastically deformed into a bent shape by pulling the first thread with forceps or the like so as to fix the first thread to the tissue. Alternatively, in a state in which the first thread is fixed to the tissue, the main body may be elastically deformed into the bent shape by pulling the second thread with the forceps or the like.

A second embodiment of the present disclosure will be described with reference to FIG. 11 and FIG. 12. In the following description, the same reference numerals will be given to the configurations common to those already described, and duplicate description will be omitted.

Figure 11:
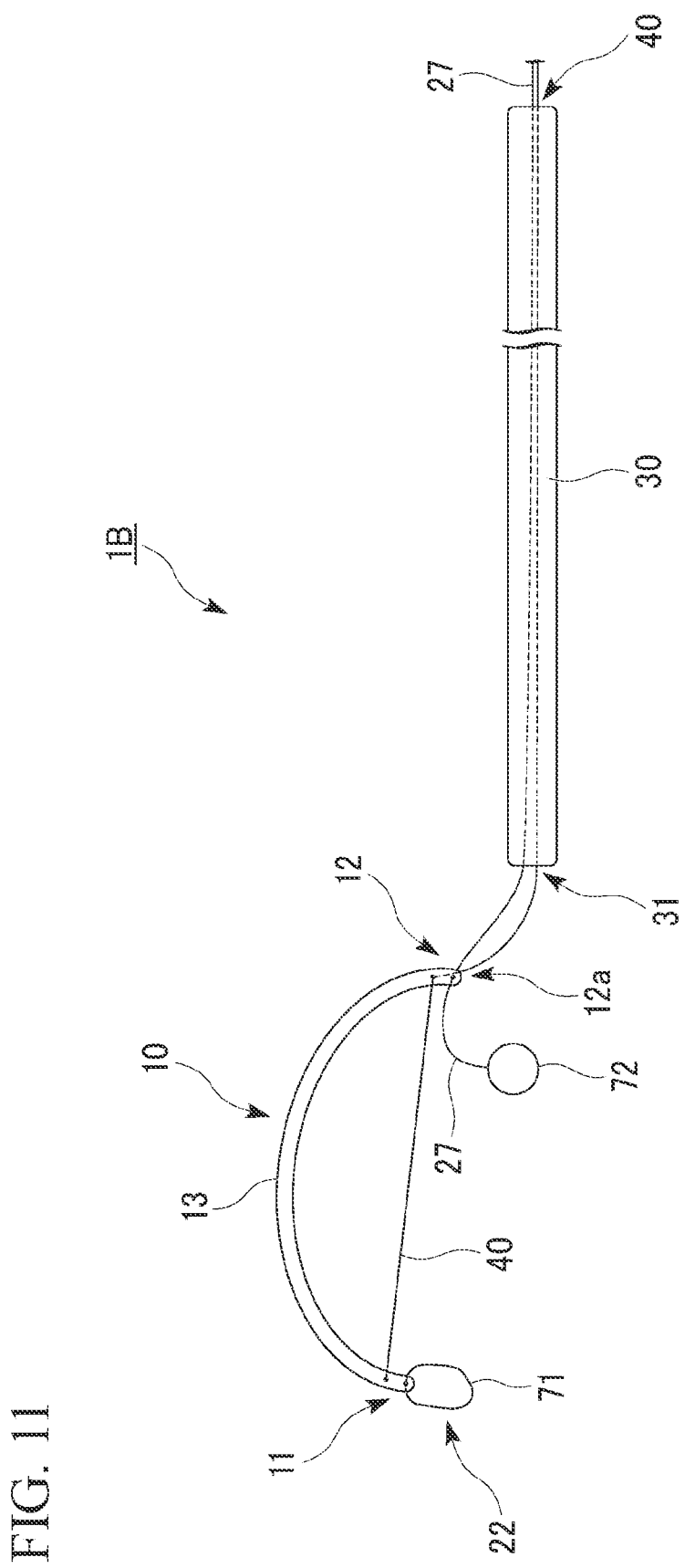
FIG. 11 is a view showing a tissue traction device according to a second embodiment of the present disclosure.

A tissue traction device 1B according to the present embodiment is shown in FIG. 11. In the tissue traction device 1B, the first fixing element and the second fixing element are a first ring 71 and a second ring 72, respectively. The first ring 71 is formed by forming the first thread 22 into a ring shape and connecting both ends to the distal end portion 11 of the main body 10. The second ring 72 is formed by forming a part of the second thread 27 into a ring shape. The second thread 27 is inserted through the sheath 30, and the second thread 27 including the second ring 72 protrudes from the distal end of the sheath 30. The second thread 27 protruding from the sheath 30 is inserted into a hole 12a formed in the proximal end portion of the main body 10 to advanceable and retractable between the second ring 72 and the distal end of the sheath 30.

Figure 12:
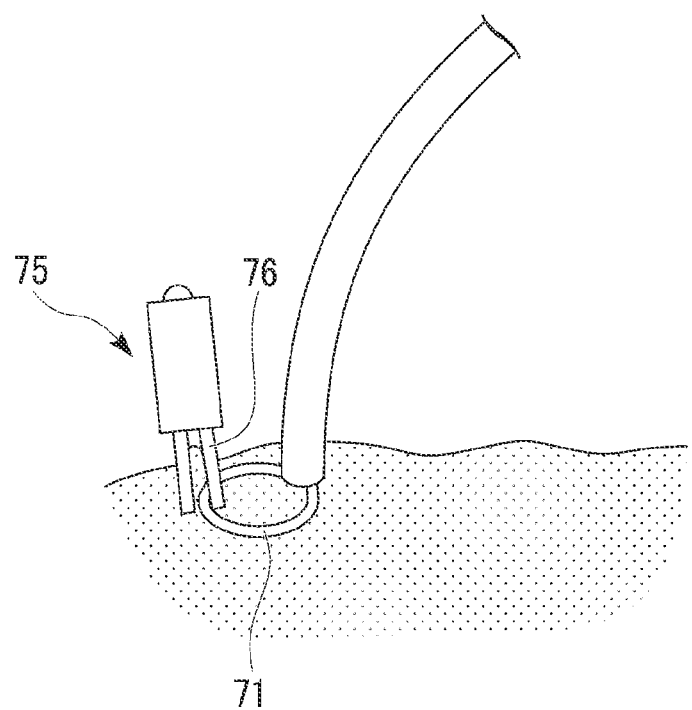
FIG. 12 is a view showing a procedure of attaching the present tissue traction device.

In the present embodiment, when the main body 10 is fixed to the tissues, the first ring 71 is positioned on the tissues, and one arm 76 of the endoscopic clip 75 is placed in the first ring 71 to make the tissues to be ligated by the clip 75, as shown in FIG. 12, the first ring 71 is locked to the tissues. Similarly, the second ring 72 can also be locked to the tissues by ligating the tissues with the clip 75 or the like.

Other operations are the same as those in the first embodiment.

The tissue traction device 1B according to the present embodiment also has the same effect as the tissue traction device 1 according to the first embodiment. Further, since the fixing elements are the first ring 71 and the second ring 72, the main body 10 can be easily fixed to the tissues.

In the present embodiment, the materials of the first ring 71 and the second ring 72 are not limited to the first thread and the second thread, however, when the first ring 71 and the second ring 72 are formed of a material that can be easily cut such as a thread or the like, the tissue traction device can be easily separated from the tissues after use.

Figure 13:
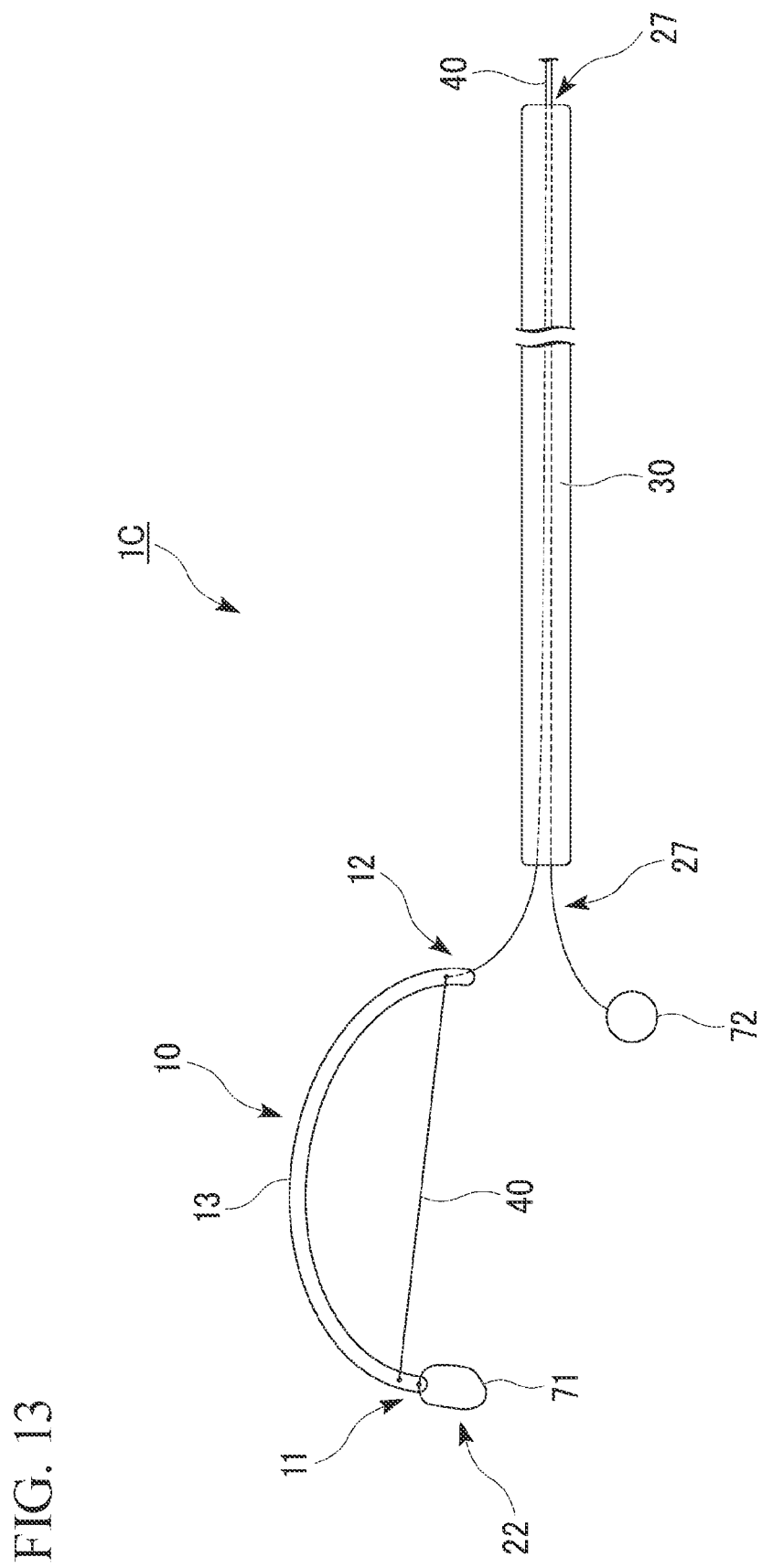
FIG. 13 is a view showing a modification example of the present tissue traction device.

In the present embodiment, the second thread 27 protruding from the distal end of the sheath 30 may not be connected to the main body 10 as in the tissue traction device 10 according to the modification example as shown in FIG. 13.

Figure 14:
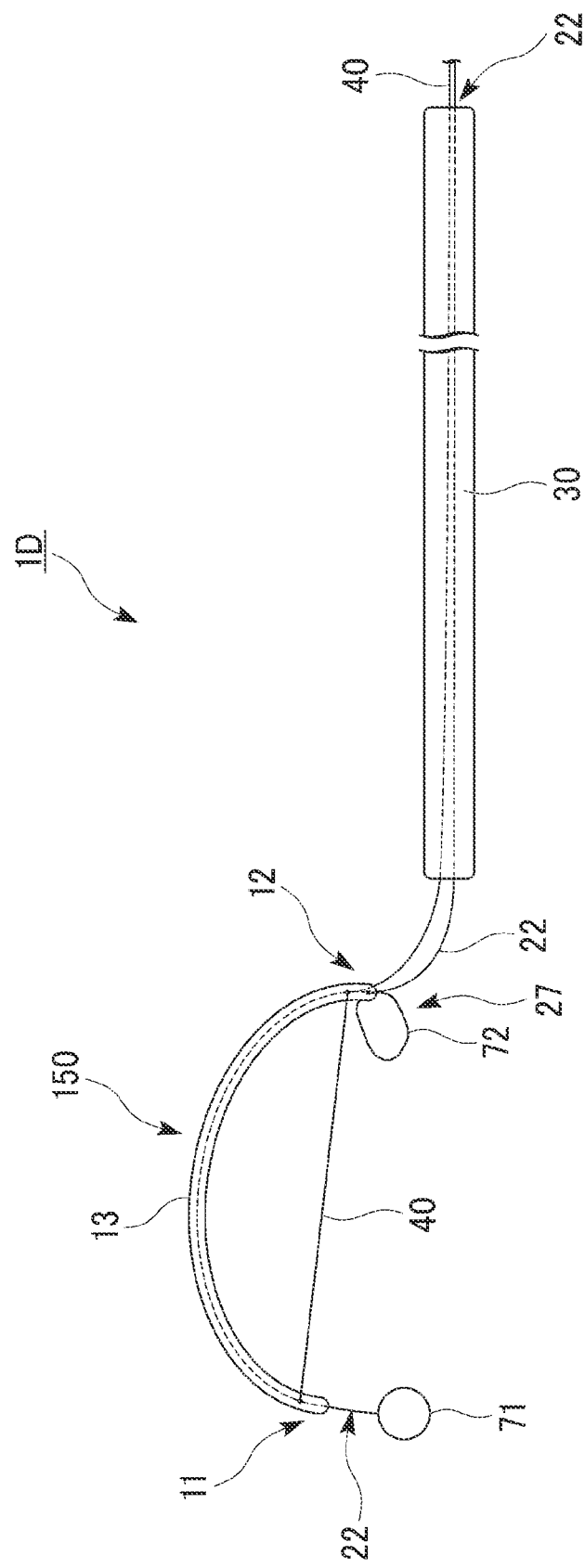
FIG. 14 is a view showing a modification example of the present tissue traction device.

The tissue traction device 1D according to the modification example as shown in FIG. 14 includes a tubular main body 150 instead of the main body 10. The first thread 22 connected to the first ring 71 passes through the main body 150 and the first thread 22 is inserted into the sheath 30 to be freely advanceable and retractable. The first thread 22 protruding from the distal end of the sheath 30 is freely advanceable and retractable with respect to the main body 150 between the first ring 71 and the distal end of the sheath 30. The second ring 72 is formed by forming the second thread 27 into a ring shape and connecting both ends to the proximal end portion 12 of the main body 150. The second thread 27 is not passed through the sheath 30.

Even with such a configuration, the same effect as that of the tissue traction device 1 according to the first embodiment can be achieved.

In this modification example, the first ring 71 may be fixed to the distal end portion 11 of the main body 10. Further, the second ring 72 and the second thread 27 may have the configurations as shown in FIG. 11 and FIG. 13.

Figure 15:
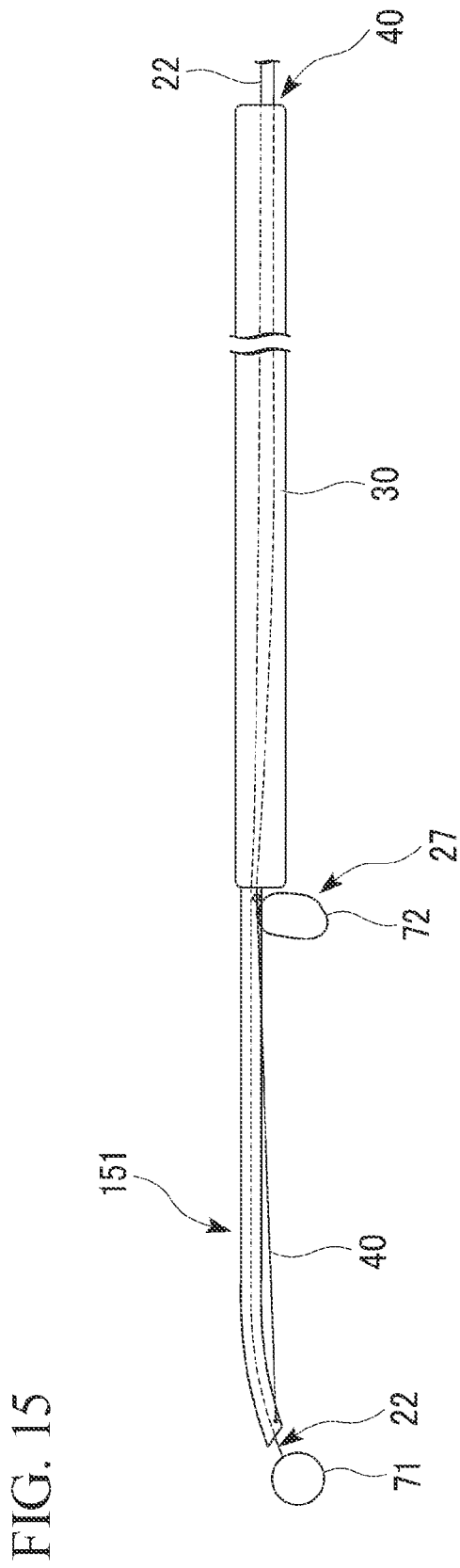
FIG. 15 is a view showing a modification example of the present tissue traction device.

In the second embodiment, the initial shape of the main body does not have to be the bent shape. For example, as shown in FIG. 15, a substantially linear main body 151 may be configured. Although an example having the equivalent configuration as that of the tissue traction device 1D is shown in FIG. 15, a substantially linear main body can be adopted in other modification examples in which the main body is not tubular.

Even in the linear main body 151, when the first thread 22 and the second thread 27 are fixed to the tissues while the main body 151 is bent, the force making the main body 151 to restore to the linear shape and the reaction force from the tissues are balanced such that the shape of the main body 151 is stable. At this time, the intermediate portion of the main body 151 is located at a position apart away from the straight line connecting the distal end portion and the proximal end portion of the main body 151.

Figure 27:
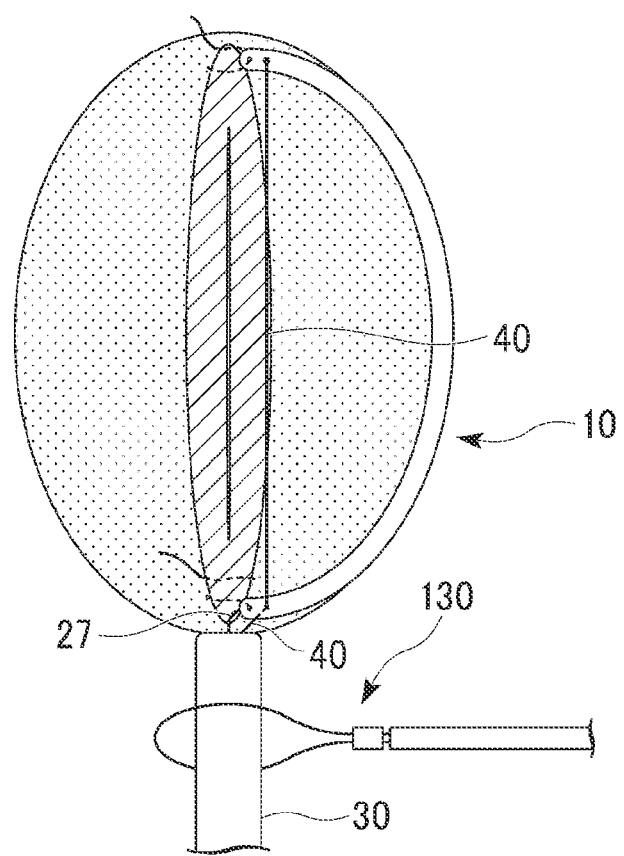
FIG. 27 is a view showing a procedure of the operation for conveniently maintaining a second bending shape.
Figure 28:
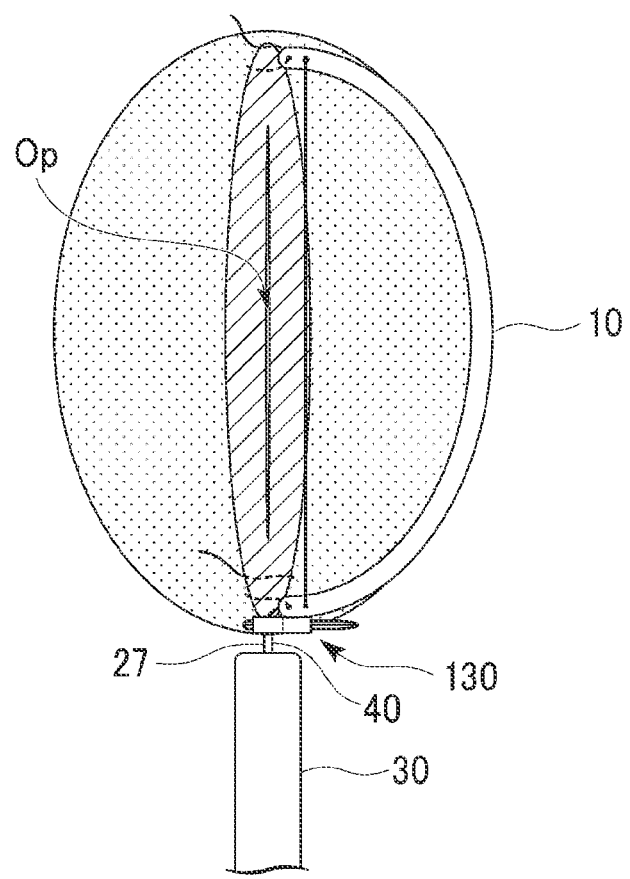
FIG. 28 is a view showing a procedure of the operation for conveniently maintaining the second bending shape.

Further, in the first and second embodiments, as shown in FIG. 27, an indwelling snare 130 may be preliminarily hooked to the sheath 30, and as shown in FIG. 28, the second thread 27 (or the evacuation thread 28) between the main body 10 and the sheath 30 in a state of stretching the opening Op may be tied with the indwelling snare 130. In this manner, even if the sheath 30 is removed from the body, the state in which the opening Op is stretched can be maintained such that the operations of the user are simplified. It is possible to maintain the same state even if the traction member 40 or the like is clamped by a clip or the like instead of the indwelling snare.

A third embodiment of the present disclosure will be described with reference to FIG. 16 to FIG. 25.

Figure 16:
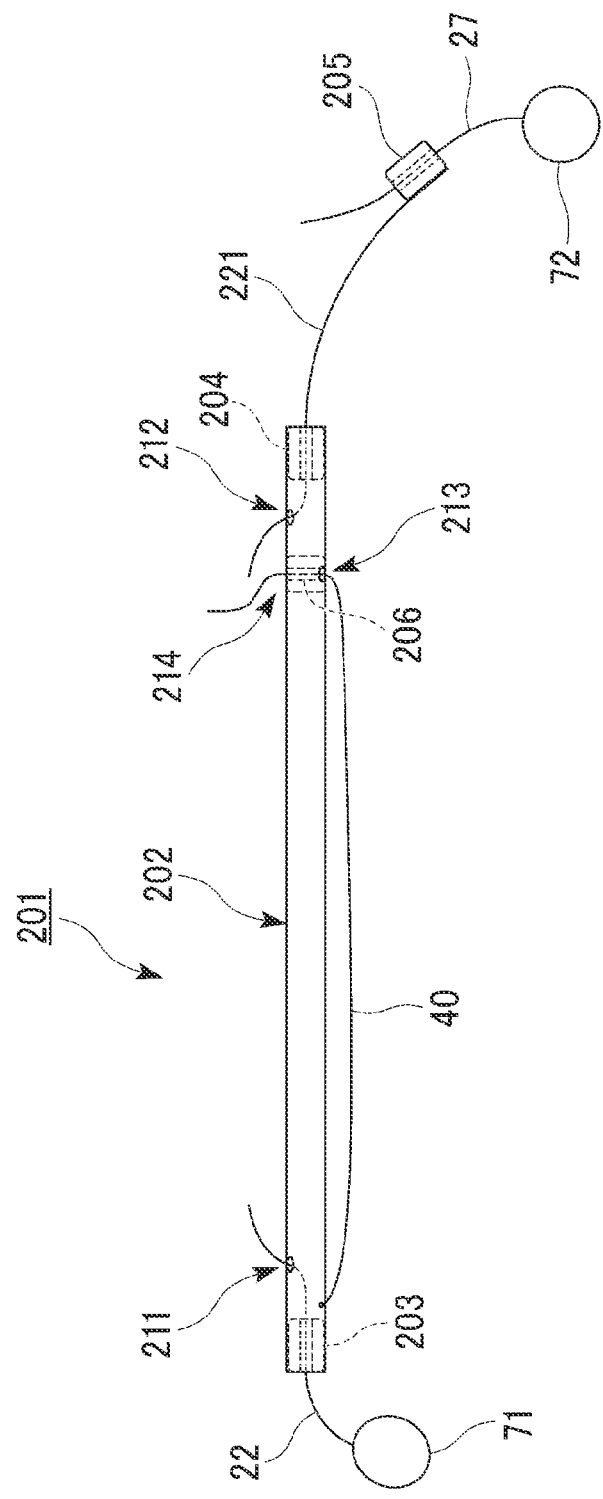
FIG. 16 is a view showing a tissue traction device according to a third embodiment of the present disclosure.

A tissue traction device 201 according to the present embodiment is shown in FIG. 16. The tissue traction device 201 includes a tubular main body 202. The outer shape of the main body 202 is substantially linear. A first holding tube 203 made of silicone or the like is fixed to the distal end portion of the main body 202. A second holding tube 204 made of silicone or the like is fixed to the proximal end portion of the main body 202.

The distal end portion of the first thread 22 forms the first ring 71, and the proximal end side thereof enters the first holding tube 203 from the distal end side of the main body 202. The first thread 22 passes through the inside of the main body 202 and is connected to the main body 202 by going out from the first opening 211 formed on the outer circumferential surface at the intermediate portion of the main body 202. The proximal end portion of the first thread 22 located outside the main body 202 can be grasped and pulled by the forceps or the like. The inner diameter of the first holding tube 203 is in the same degree as the diameter of the first thread 22, and the first thread 22 passing through the first holding tube 203 causes friction with the inner surface of the first holding tube 203 and the first thread 22 is frictionally engaged with the first holding tube 203. The first thread 22 is slidable in the main body 202 while causing friction with the first holding tube 203.

The distal end portion of the second thread 27 forms the second ring 72, and the proximal end side is passed through the third holding tube 205. Similar to the first thread 22, the second thread 27 passing through the third holding tube 205 causes friction with the inner surface of the third holding tube 205 and the second thread 27 is frictionally engaged with the third holding tube 205. The second thread 27 is slidable in the third holding tube 205 while causing friction with the third holding tube 205.

A first end portion of the evacuation thread 221 is fixed to the outer circumferential surface of the third holding tube 205. A second end portion of the evacuation thread 221 has entered the second holding tube 204 from the proximal end side of the main body 202. The evacuation thread 221 passes through the inside of the main body 202 and is connected to the main body 202 by going out from a second opening 212 formed on the outer circumferential surface at the intermediate portion of the main body 202. The second opening 212 is located on the proximal end side of the first opening 211 and on the distal end side of the second holding tube 204. Similar to the first thread 22, the evacuation thread 221 passing through the second holding tube 204 causes friction with the inner surface of the second holding tube 204 and the evacuation thread 21 is frictionally engaged with the second holding tube 204. The evacuation thread 221 is slidable in the main body 202 while causing friction with the second holding tube 204.

The distal end of the traction member 40 is fixed to the outer circumferential surface of the distal end portion of the main body 202. The traction member 40 enters the main body 202 from a third opening 213 formed on the outer circumferential surface of the proximal end portion of the main body 202, and goes out of the main body 202 from a fourth opening 214 formed on the outer circumferential surface of the proximal end portion of the main body 202. A fourth holding tube 206 made of silicone or the like is arranged in the main body 202. A lumen of the fourth holding tube 206 extends in a direction connecting the third opening 213 and the fourth opening 214, and the lumen communicates with the third opening 213 and the fourth opening 214. The traction member 40 is slidable in the fourth holding tube 206 between the third opening 213 and the fourth opening 214, and the traction member 40 is frictionally engaged with the fourth holding tube 206.

The operation when the tissue traction device 201 is used will be described.

The user determines the positions of the first fixation site and the second fixation site for fixing the first ring 71 and the second ring 72 in the surrounding tissues ST of the region R by the same procedures as those in the first embodiment.

Figure 17:
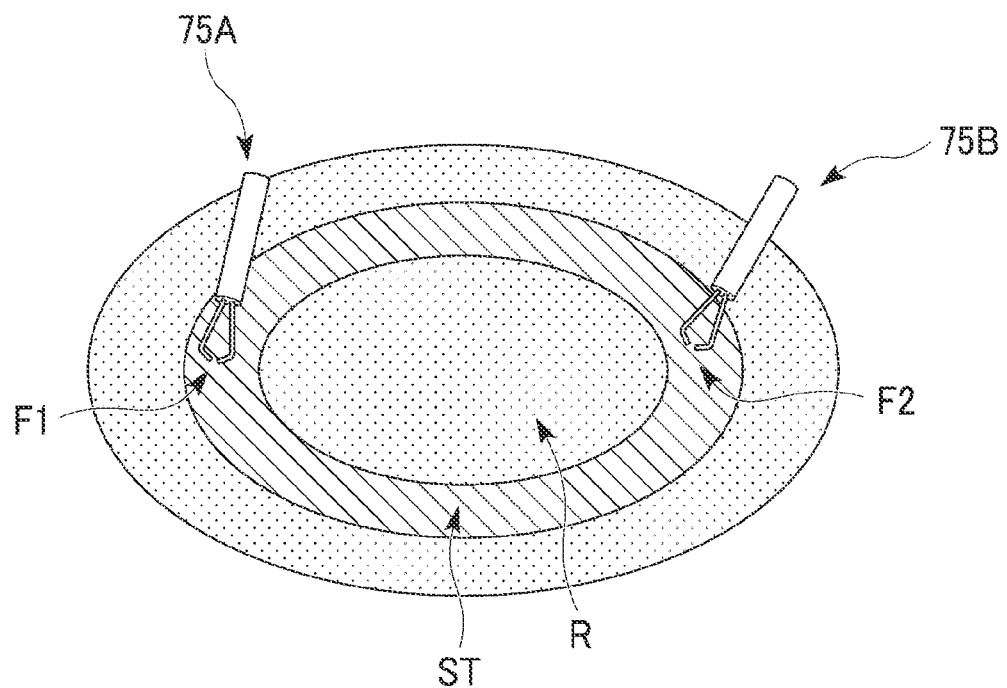
FIG. 17 is a view showing a procedure of using the present tissue traction device.

As shown in FIG. 17, the user indwells a clip 75A and a clip 75B at the first fixation site F1 and the second fixation site F2, respectively.

Subsequently, the tissue traction device 201 is introduced into the body. Since the main body 202 is substantially linear, the endoscope 100 and the tissue traction device 1 can be introduced into the body through the mouth or the like with a part of the main body 202 inserted into the channel from the distal end of the endoscope 100.

Figure 18:
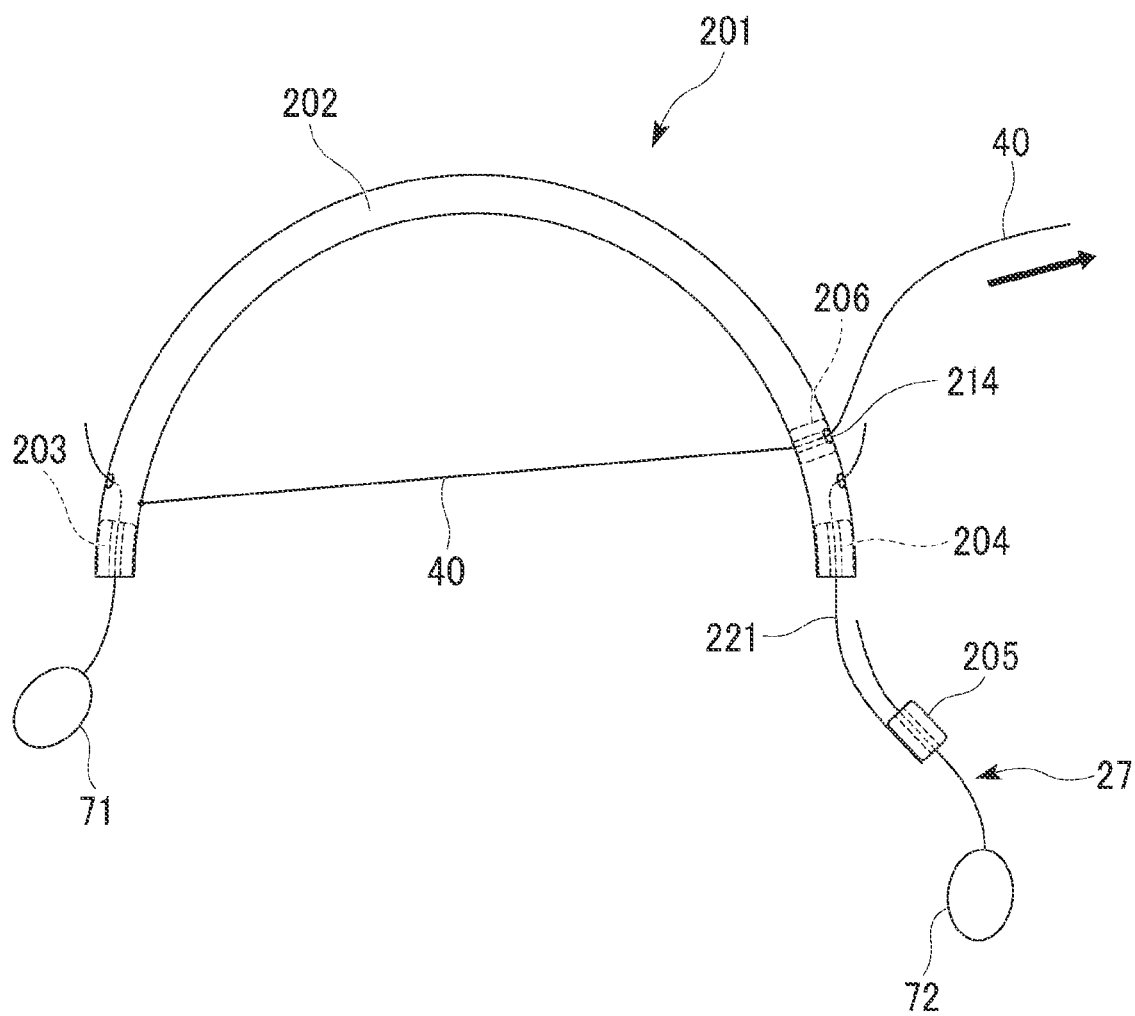
FIG. 18 is a view showing a procedure of using the present tissue traction device.

When the endoscope 100 and the tissue traction device 1 reach the vicinity of the area R, the user pulls the proximal end portion of the traction member 40. Then, the traction member 40 moves in the fourth holding tube 206 and the traction member 40 is pulled out from the fourth opening 214. When the traction procedure is released, the traction member 40 and the fourth holding tube 206 are frictionally engaged with each other, and the positional relationship between the traction member 40 and the fourth holding tube 206 is maintained. As a result, as shown in FIG. 18, the main body 202 is elastically deformed into a bent shape, and the intermediate portion of the main body 202 moves to a position apart away from the straight line connecting the distal end portion and the proximal end portion of the main body 202.

Figure 19:
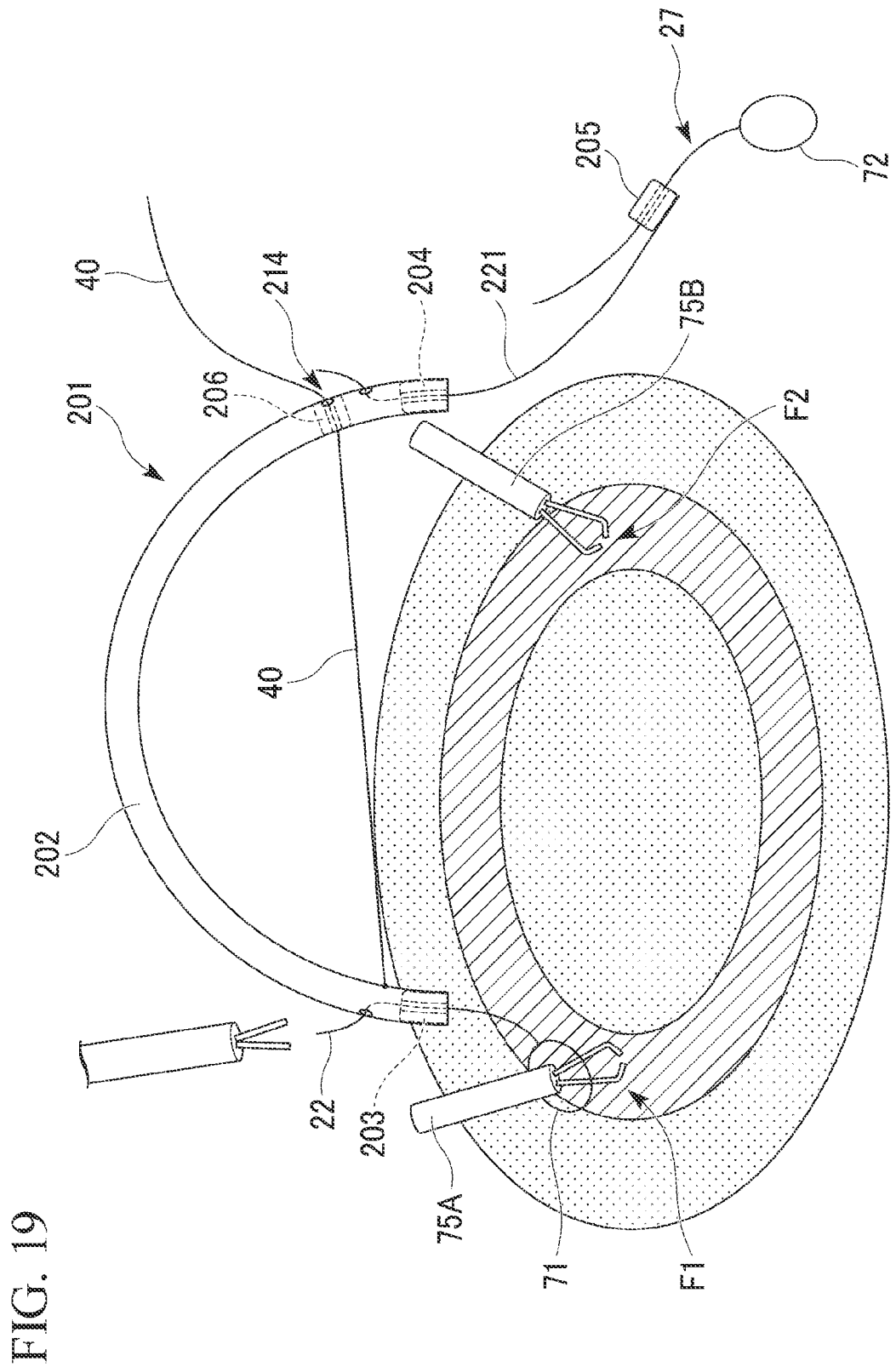
FIG. 19 is a view showing a procedure of using the present tissue traction device.
Figure 20:
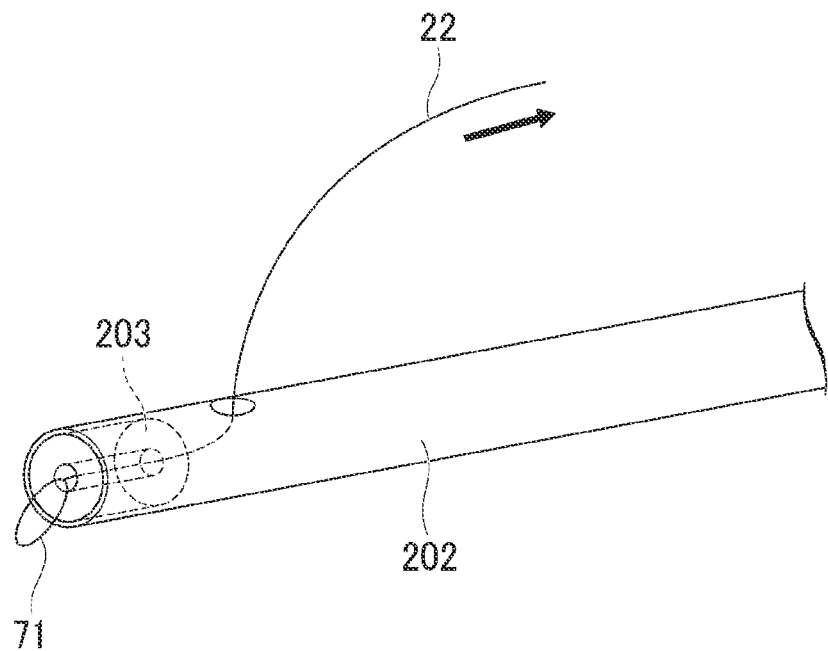
FIG. 20 is a view showing a procedure of using the present tissue traction device.
Figure 21:
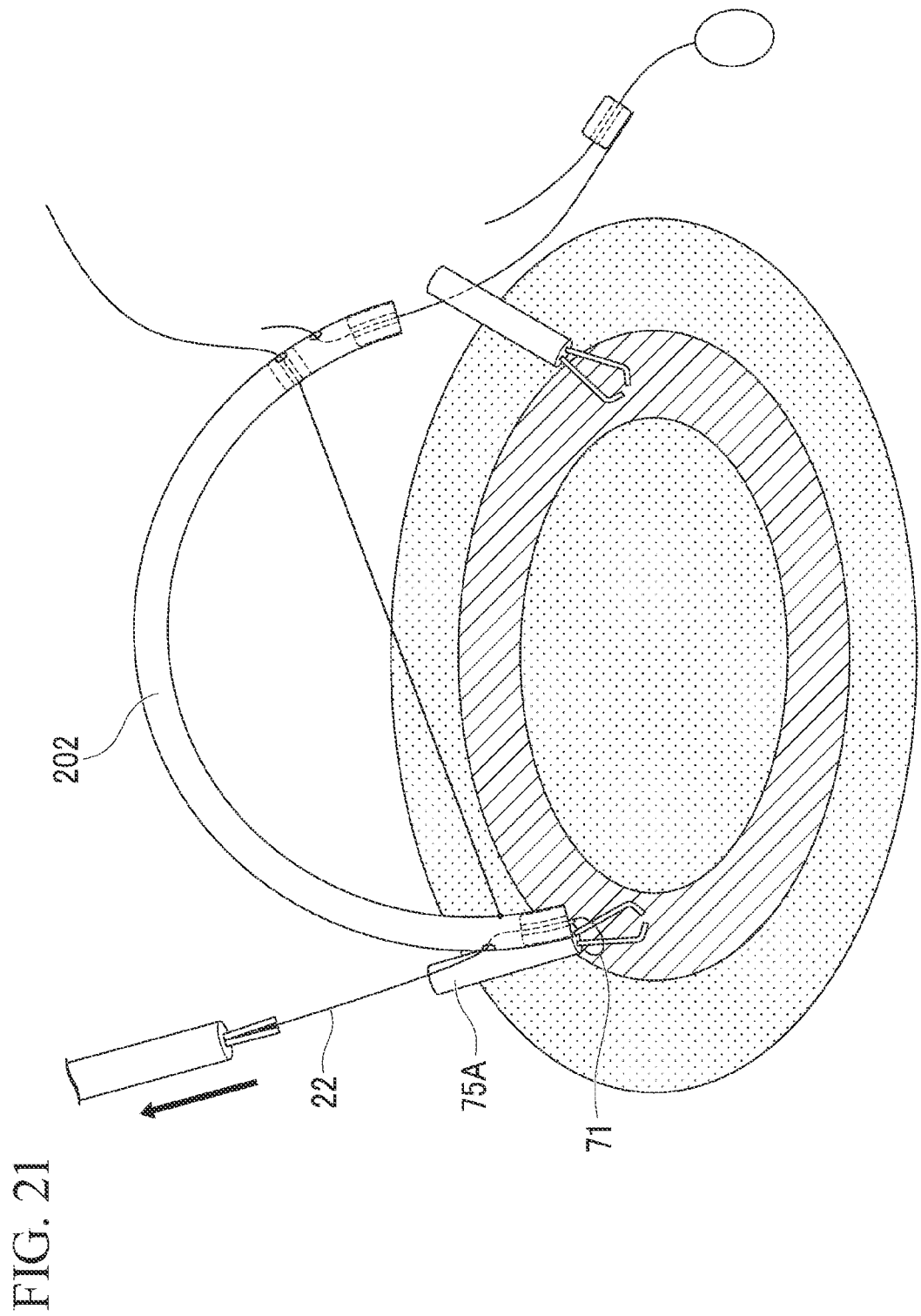
FIG. 21 is a view showing a procedure of using the present tissue traction device.

Next, as shown in FIG. 19, the user hooks the first ring 71 on the clip 75A indwelled at the first fixation site F1. When the proximal end portion of the first thread 22 is pulled with forceps or the like in this state, the first ring 71 moves toward the main body 202 as shown in FIG. 20, and a part of the first ring 71 moves into the first holding tube 203. As a result, as shown in FIG. 21, the first ring 71 is locked so as not to slip off from the clip 75A and the distal end portion of the main body 202 is supported by the clip 75A.

Figure 22:
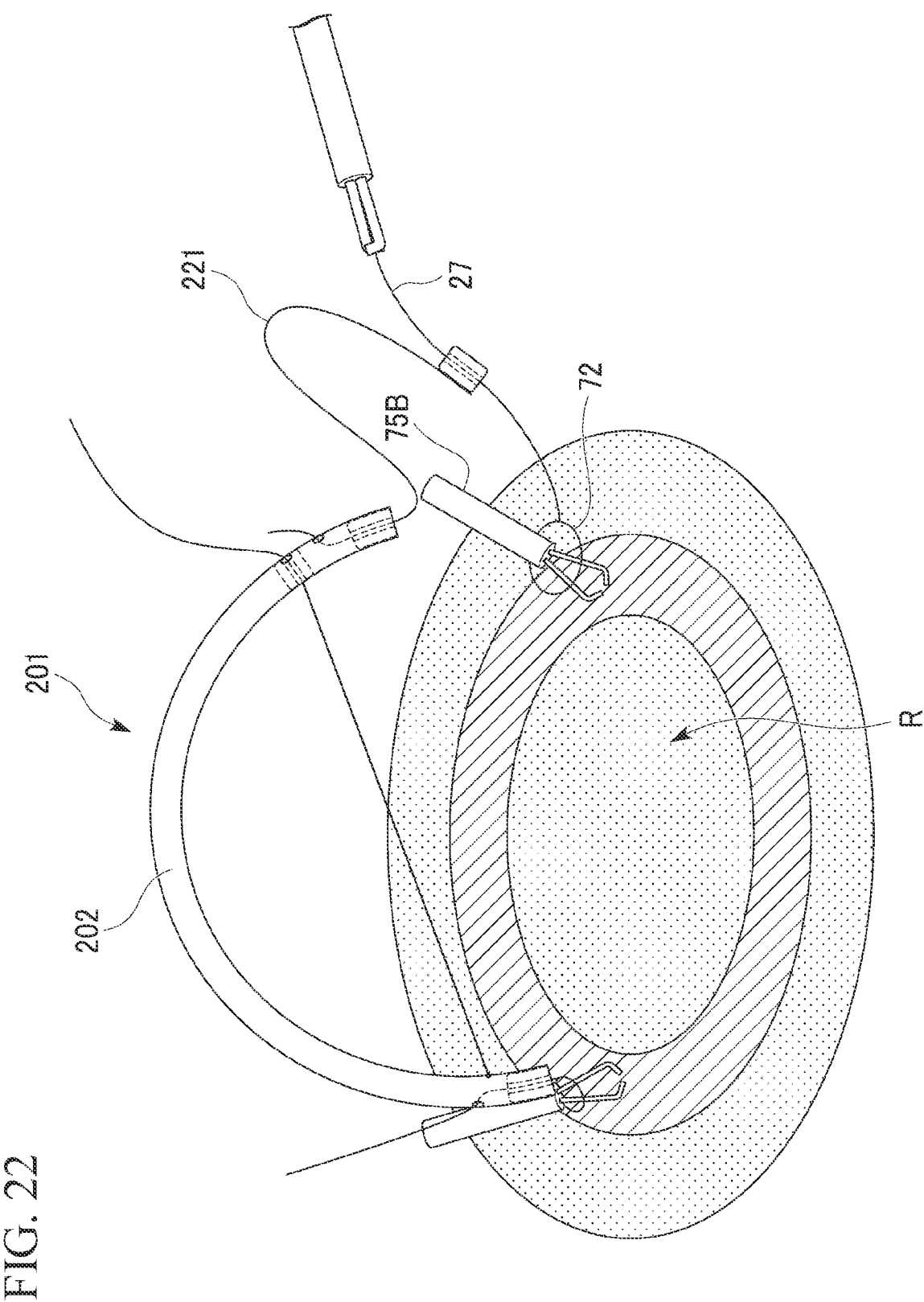
FIG. 22 is a view showing a procedure of using the present tissue traction device.
Figure 23:
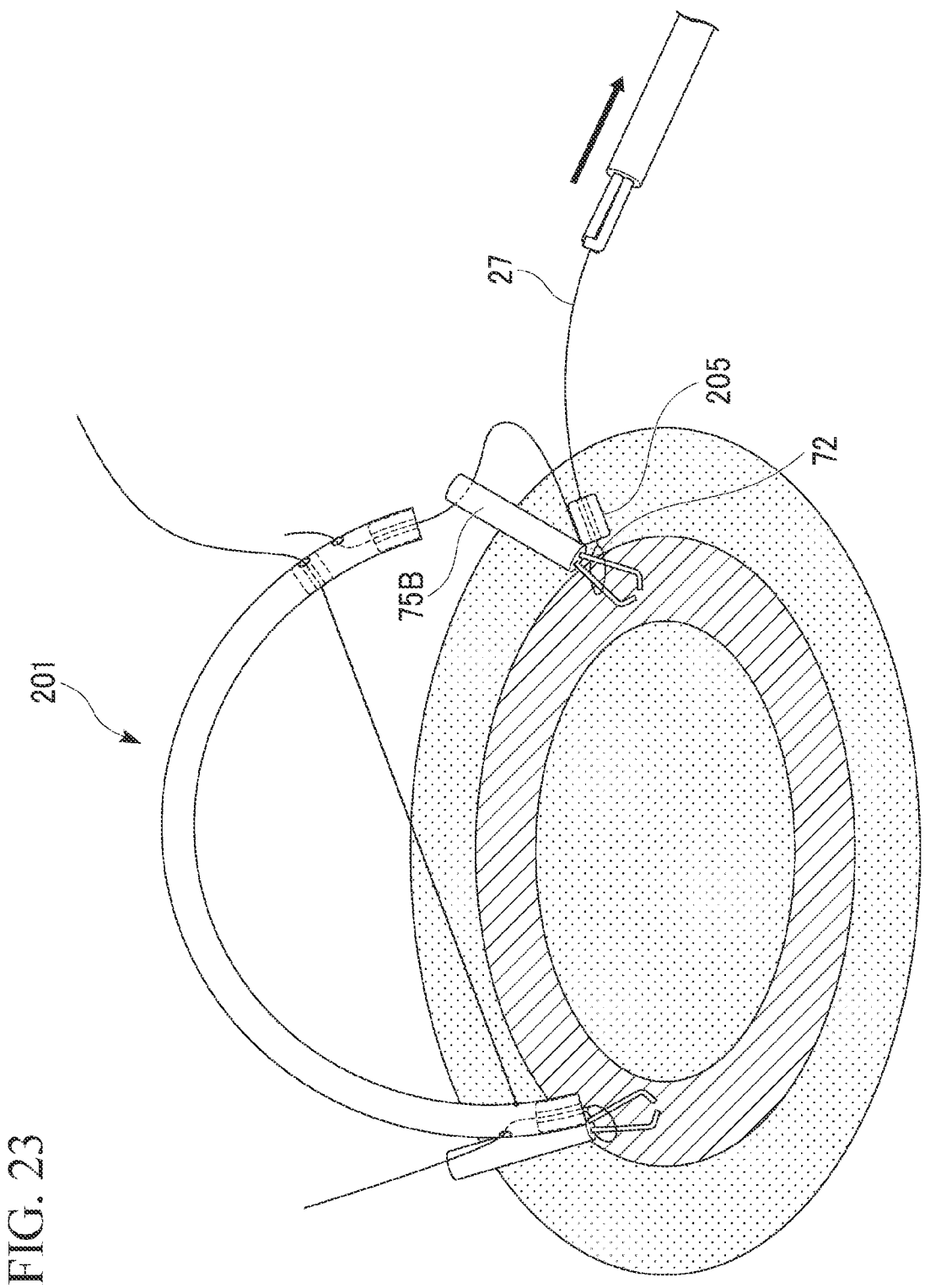
FIG. 23 is a view showing a procedure of using the present tissue traction device.

The user hooks the second ring 72 on the clip 75B and pulls the proximal end portion of the second thread 27 in the same procedures as shown in FIG. 22. As a result, as shown in FIG. 23, the second ring 72 is locked so as not to slip off from the clip 75B. The state in which the second ring 72 is locked to the clip 75B is maintained by the frictional engagement between the second thread 27 and the third holding tube 205. In a state in which the first ring 71 and the second ring 72 are fixed to the tissues, the intermediate portion of the main body 202 is located at a position apart away from the straight line connecting the distal end portion and the proximal end portion of the main body 202.

As described above, the attachment procedure of the tissue traction device 201 to the gastrointestinal wall is finished.

Since the second ring 72 and the main body 202 are connected by the evacuation thread 221, the user can move the main body 202 within a certain range so as to smoothly proceed with the tissue resection procedure or the like with respect to the region R.

Figure 24:
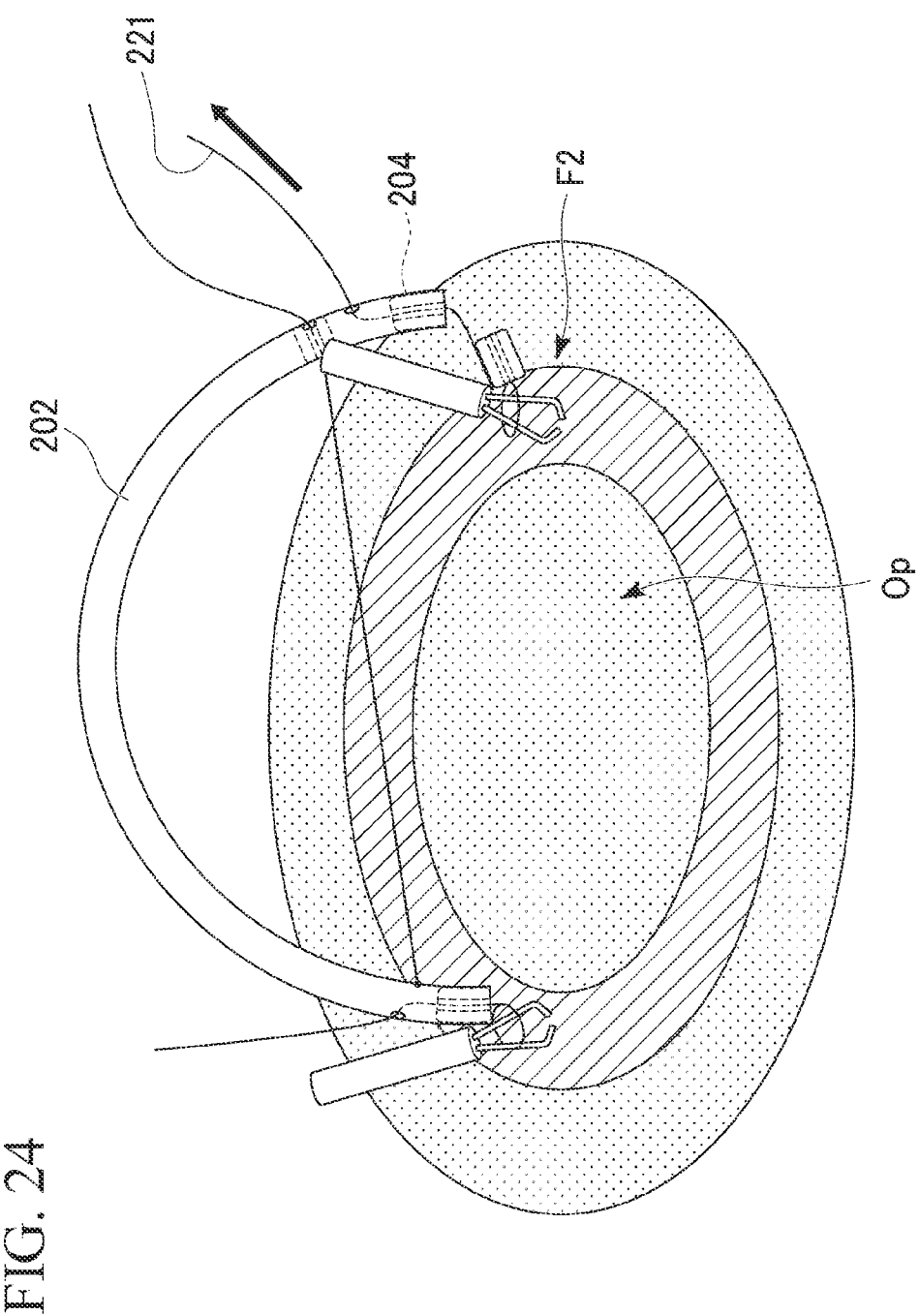
FIG. 24 is a view showing a procedure of using the present tissue traction device.

After forming the opening Op in the region R, as shown in FIG. 24, the proximal end portion of the evacuation thread 221 is pulled by forceps or the like to make the proximal end portion of the main body 202 to approach the second fixation site F2. The state in which the proximal end portion of the main body 202 is close to the second fixation site F2 is maintained due to the frictional engagement between the evacuation thread 221 and the second holding tube 204.

Figure 25:
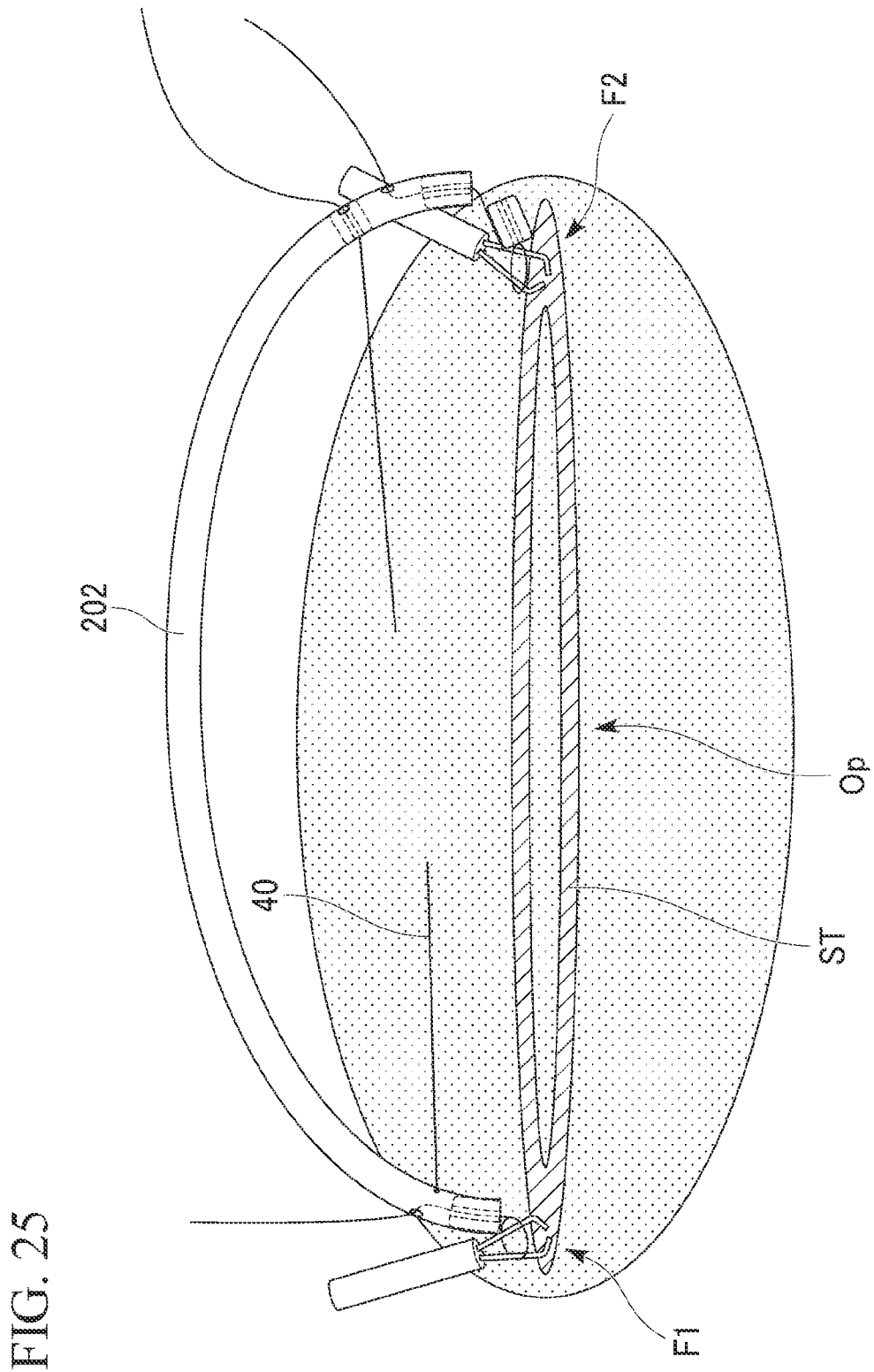
FIG. 25 is a view showing a procedure of using the present tissue traction device.

Thereafter, when the user cuts off the traction member 40, the main body 202 tends to return to the substantially linear shape by its own restoring force, as shown in FIG. 25. Such restoring force applies on the first fixation site F1 and the second fixation site F2. As a result, the first fixation site F1 and the second fixation site F2 move to be separated from each other. When the first fixed portion F1 and the second fixed portion F2 are separated from each other, the opening Op is stretched in the direction connecting the first fixation site F1 and the second fixation site F2 and deformed into the elongated shape such that the surrounding tissues ST being opposite to each other and sandwiching the opening Op also approach each other. The main body 202 maintains the state in which the opening Op is stretched against the reaction force received from the tissues.

The tissue traction device 201 according to the present embodiment also has the same effect as the tissue traction device 1 according to the first embodiment.

Figure 26:
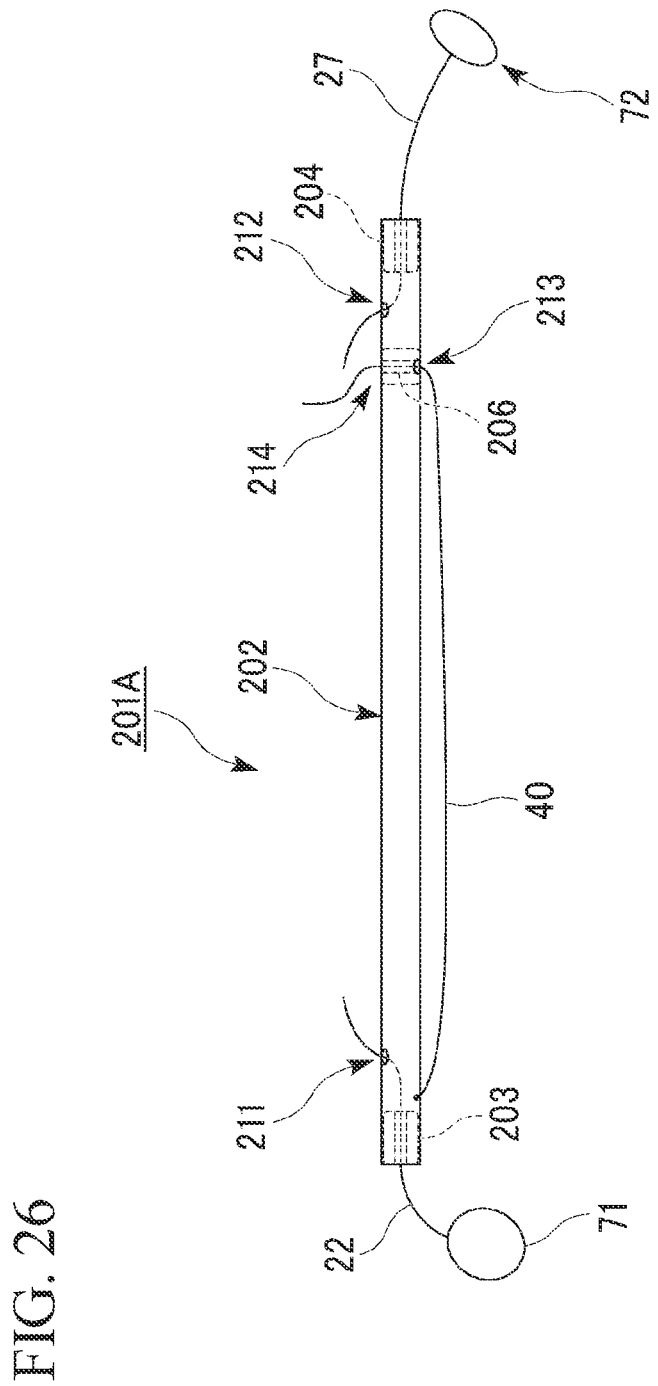
FIG. 26 is a view showing a modification example of the present tissue traction device.

It is not necessary for the tissue traction device according to the present embodiment to include the evacuation thread. In a tissue traction device 201A according to the modification example as shown in FIG. 26, the second thread 27 and the main body 202 are connected by the second thread 27 passing through the second holding tube 204 of the main body 202 and being pulled out from the second opening 212.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A tissue traction device, comprising:
a first needle connected to a distal end of a first thread;
a second needle connected to a distal end of a second thread;
an elongated main body connected to the first thread and extending between the first thread and the second thread, the main body being elastically deformable;
a tube disposed at a proximal end of the main body;
a traction member having a distal end connected to a distal end portion of the main body, the traction member extending from the distal end portion of the main body toward a distal end of the tube;
wherein the main body includes an intermediate portion between the distal end portion of the main body and a proximal end portion of the main body, and
when the traction member is pulled while a distal end of the tube is in contact with the proximal end portion, the intermediate portion is elastically deformed to a bent shape.

2. The tissue traction device according to claim 1, wherein the main body is connected to a proximal end of the first thread, and the main body extends between the proximal end of the first thread and a proximal end of the second thread.

3. The tissue traction device according to claim 1, wherein part of the traction member is inserted into the tube from a distal end portion of the tube and goes out from a proximal end portion of the tube.

4. The tissue traction device according to claim 1, wherein the main body has a hole, and the traction member is inserted through the hole to be advanceable and retractable.

5. The tissue traction device according to claim 1, wherein the tube has a hole, and the traction member is inserted through the hole to be advanceable and retractable.

6. The tissue traction device according to claim 1,
wherein the main body includes an intermediate portion between the distal end portion of the main body and the proximal end portion of the main body, and
the intermediate portion is at a position apart away from a straight line connecting the distal end portion and the proximal end portion in a state in which the first thread and the second thread are hooked to the tissues.

7. The tissue traction device according to claim 1,
wherein the main body includes an intermediate portion between the distal end portion of the main body and the proximal end portion of the main body, and
the intermediate portion is at a position apart away from a straight line connecting the distal end portion and the proximal end portion in a state in which the main body is in an elastically deformed state.

8. The tissue traction device according to claim 1, further includes an evacuation thread connected to the first thread or the second thread, and the evacuation thread is able to pass through the tube to be advanceable and retractable.

9. The tissue traction device according to claim 1, wherein the tube has a hole, and the traction member is inserted through the hole to be advanceable and retractable.

10. A tissue traction device, comprising:
a first thread;
a second thread;
an elongated main body connected to the first thread and extending between the first thread and the second thread, the main body being elastically deformable;
a tube disposed at a proximal end of the main body;
a traction member having a distal end connected to a distal end portion of the main body, the traction member extending from the distal end portion of the main body toward a distal end of the tube, wherein the first thread includes a first ring, and
the second thread includes a second ring that protrudes from the tube;
wherein the main body includes an intermediate portion between the distal end portion of the main body and a proximal end portion of the main body, and
when the traction member is pulled while a distal end of the tube is in contact with the proximal end portion, the intermediate portion is elastically deformed to a bent shape.

11. The tissue traction device according to claim 10, wherein the main body is connected to a proximal end of the first thread, and the main body extends between the proximal end of the first thread and a proximal end of the second thread.

12. The tissue traction device according to claim 10, wherein part of the traction member is inserted into the tube from a distal end portion of the tube and goes out from a proximal end portion of the tube.

13. The tissue traction device according to claim 10, wherein the main body has a hole, and the traction member is inserted through the hole to be advanceable and retractable.

14. The tissue traction device according to claim 10, wherein part of the traction member is inserted through the main body to be slidable, and a proximal end portion of the traction member protrudes from the main body.

15. The tissue traction device according to claim 10,
wherein part of the first thread is inserted through the main body to be slidable,
a proximal end portion of the first thread protrudes from the main body, and
when the proximal end portion of the first thread is pulled, part of the first ring is moved into the main body.

16. The tissue traction device according to claim 15, further includes an evacuation thread connected to a holding tube,
wherein the second ring is formed in a distal end portion of the second thread,
the second thread is inserted through the holding tube to be slidable, and
part of the evacuation thread is inserted through the main body to be slidable, and a proximal end portion of the evacuation thread protrudes from the main body.

17. The tissue traction device according to claim 10,
wherein the main body includes an intermediate portion between the distal end portion of the main body and the proximal end portion of the main body, and
the intermediate portion is at a position apart away from a straight line connecting the distal end portion and the proximal end portion in a state in which the first thread and the second thread are hooked to the tissues.

18. The tissue traction device according to claim 10,
wherein the main body includes an intermediate portion between the distal end portion of the main body and the proximal end portion of the main body, and
the intermediate portion is at a position apart away from a straight line connecting the distal end portion and the proximal end portion in a state in which the main body is in an elastically deformed state.

* * * * *